United States Patent
Roth et al.

(10) Patent No.: US 12,164,073 B2
(45) Date of Patent: Dec. 10, 2024

(54) CALIBRATION AND QUALITY CONTROL OF A NUCLEAR-MEDICINE (N-M) RADIO IMAGING SYSTEM

(71) Applicant: Spectrum Dynamics Medical Limited, Road Town (VG)

(72) Inventors: Nathaniel Roth, Tel-Aviv (IL); Yoel Zilberstien, Herzlia (IL)

(73) Assignee: Spectrum Dynamics Medical Limited, Road Town (VG)

( * ) Notice: Subject to any disclaimer, the term of this patent is extended or adjusted under 35 U.S.C. 154(b) by 116 days.

(21) Appl. No.: 17/676,269

(22) Filed: Feb. 21, 2022

(65) Prior Publication Data

US 2022/0179109 A1    Jun. 9, 2022

Related U.S. Application Data

(63) Continuation of application No. 16/756,496, filed as application No. PCT/IB2018/058108 on Oct. 18, 2018, now Pat. No. 11,255,987.

(60) Provisional application No. 62/574,300, filed on Oct. 19, 2017.

(51) Int. Cl.
| | | |
|---|---|---|
| *G01T 1/161* | (2006.01) | |
| *A61B 6/00* | (2006.01) | |
| *G01T 7/00* | (2006.01) | |
| *G06T 7/80* | (2017.01) | |

(52) U.S. Cl.
CPC ............ *G01T 7/005* (2013.01); *A61B 6/5258* (2013.01); *G06T 7/80* (2017.01); *G06T 2207/10104* (2013.01); *G06T 2207/10108* (2013.01)

(58) Field of Classification Search
CPC .................................................. A61B 6/5258
See application file for complete search history.

(56) References Cited

U.S. PATENT DOCUMENTS

| | | | |
|---|---|---|---|
| 3,902,070 | A | 8/1975 | AmorJr et al. |
| 4,057,726 | A | 11/1977 | Jaszczak |
| 4,209,700 | A | 6/1980 | Stoddart |
| 5,740,222 | A | 4/1998 | Fujita et al. |
| 5,982,843 | A | 11/1999 | Bailey et al. |
| 6,140,650 | A | 10/2000 | Berlad |
| 6,188,743 | B1 | 2/2001 | Tybinkowski et al. |
| 6,212,251 | B1 | 4/2001 | Tomura et al. |
| 6,242,743 | B1 | 6/2001 | DeVito et al. |

(Continued)

FOREIGN PATENT DOCUMENTS

| | | |
|---|---|---|
| EP | 0 283 870 | 10/1990 |
| WO | WO 2013/168111 | 11/2013 |

(Continued)

OTHER PUBLICATIONS

Notice of Allowance Dated Jun. 1, 2022 from US Patent and Trademark Office Re. U.S. Appl. No. 17/120,394. (7 pages).

(Continued)

*Primary Examiner* — David P Porta
*Assistant Examiner* — Shun Lee

(57) ABSTRACT

Methods for calibrating a Nuclear-Medicine (N-M) imaging system including calibrating an N-M imaging system scanning unit for scanning detector uniformity map and energy resolution as well as generating an angular orientation map of a plurality of scanning units and a line source of radiation. There is further disclosed a jig for holding a line source during a calibration process of an N-M imaging system.

24 Claims, 15 Drawing Sheets

(56) References Cited

U.S. PATENT DOCUMENTS

| | | |
|---|---|---|
| 6,472,668 B1 | 10/2002 | Griesmer et al. |
| 6,583,420 B1 | 6/2003 | Nelson et al. |
| 6,988,827 B2 | 1/2006 | Mueller |
| 7,030,387 B2 | 4/2006 | Serebryanov et al. |
| 7,201,515 B2 | 4/2007 | Lacey |
| 7,262,415 B2 | 8/2007 | Crosetto |
| 7,342,234 B2 | 3/2008 | Yanagita et al. |
| 7,488,949 B2 | 2/2009 | Ueno et al. |
| 7,511,277 B2 | 3/2009 | Ueno et al. |
| 7,573,040 B2 | 8/2009 | Tkaczyk et al. |
| 7,592,597 B2 | 9/2009 | Hefetz et al. |
| 7,755,057 B2 | 7/2010 | Kim |
| 7,772,559 B2 | 8/2010 | Burbar et al. |
| 8,269,176 B2 | 9/2012 | D'Ambrosio et al. |
| 8,338,788 B2 | 12/2012 | Zilberstein et al. |
| 8,378,677 B2 | 2/2013 | Morich et al. |
| 8,409,092 B2 | 4/2013 | Canzolino |
| 8,476,594 B2 | 7/2013 | Frach |
| 8,481,949 B2 | 7/2013 | Martin |
| 8,492,725 B2 | 7/2013 | Zilberstein et al. |
| 8,699,660 B2 | 4/2014 | Joshi et al. |
| 8,748,827 B2 | 6/2014 | Zilberstein et al. |
| 8,987,673 B2 | 3/2015 | Niederöhner et al. |
| 9,029,791 B1 | 5/2015 | Kowalski et al. |
| 9,057,788 B2 | 6/2015 | Abraham et al. |
| 9,173,618 B2 | 11/2015 | Hermony |
| 9,295,439 B2 | 3/2016 | Hefetz |
| 9,513,236 B2 | 12/2016 | Kawaguchi et al. |
| 9,579,072 B1 | 2/2017 | Grobshtein et al. |
| 9,599,490 B2 | 3/2017 | Khen et al. |
| 9,606,245 B1 | 3/2017 | Czarnecki et al. |
| 9,662,079 B2 | 5/2017 | Rafaeli et al. |
| 9,700,273 B2 | 7/2017 | Lacey et al. |
| 9,820,708 B2 | 11/2017 | Risher-Kelly |
| 9,869,647 B2 | 1/2018 | Featonby et al. |
| 9,903,964 B2 | 2/2018 | Thran |
| 9,924,915 B2 | 3/2018 | Kodaira |
| 10,054,698 B2 | 8/2018 | Hefetz et al. |
| 10,143,437 B2 | 12/2018 | Hefetz et al. |
| 10,178,976 B2 | 1/2019 | Liu |
| 10,253,903 B2 | 4/2019 | Fujimoto et al. |
| 10,267,930 B2 | 4/2019 | Su et al. |
| 10,326,561 B2 | 6/2019 | Dudek et al. |
| 10,441,816 B2 | 10/2019 | Liu et al. |
| 10,478,133 B2 | 11/2019 | Levy et al. |
| 10,488,533 B2 | 11/2019 | Liu et al. |
| 10,542,228 B2 | 1/2020 | Nozawa et al. |
| 10,575,802 B2 | 3/2020 | Bouhnik et al. |
| 10,624,596 B2 | 4/2020 | Gregerson et al. |
| 10,663,608 B2 | 5/2020 | Lyu et al. |
| 10,716,955 B2 | 7/2020 | Kuang et al. |
| 10,772,590 B2 | 9/2020 | Arber et al. |
| 10,863,956 B2 | 12/2020 | Zilberstein et al. |
| 10,987,069 B2 | 4/2021 | Roth |
| 11,006,911 B2 | 5/2021 | Liu et al. |
| 11,020,074 B2 | 6/2021 | Kenig et al. |
| 11,255,987 B2 | 2/2022 | Roth et al. |
| 11,311,254 B2 | 4/2022 | Okuno |
| 11,337,660 B2 | 5/2022 | Zilberstien et al. |
| 11,585,953 B2 | 2/2023 | Ye et al. |
| 2003/0209662 A1 | 11/2003 | Nelson et al. |
| 2005/0017182 A1 | 1/2005 | Joung et al. |
| 2008/0217541 A1 | 9/2008 | Kim |
| 2008/0230709 A1 | 9/2008 | Tkaczyk et al. |
| 2010/0061509 A1 | 3/2010 | D'Ambrosio et al. |
| 2010/0188082 A1 | 7/2010 | Morich et al. |
| 2011/0026685 A1 | 2/2011 | Zilberstein et al. |
| 2011/0103544 A1 | 5/2011 | Hermony |
| 2013/0168567 A1 | 7/2013 | Wartski et al. |
| 2013/0200269 A1 | 8/2013 | Abraham et al. |
| 2013/0343507 A1 | 12/2013 | Gregerson |
| 2014/0270051 A1 | 9/2014 | Smithanik |
| 2015/0028218 A1 | 1/2015 | Kataoka et al. |
| 2015/0065874 A1 | 3/2015 | Rafaeli et al. |
| 2015/0094571 A1 | 4/2015 | Bouhnik et al. |
| 2015/0119704 A1 | 4/2015 | Roth et al. |
| 2015/0276949 A1 | 10/2015 | Grobshtein et al. |
| 2015/0342543 A1 | 12/2015 | Khen et al. |
| 2016/0007941 A1 | 1/2016 | Hefetz |
| 2016/0282153 A1 | 9/2016 | Hefetz et al. |
| 2016/0287197 A1 | 10/2016 | Risher-Kelly et al. |
| 2016/0313263 A1 | 10/2016 | Featonby et al. |
| 2016/0380728 A1 | 12/2016 | Dudek et al. |
| 2017/0014096 A1 | 1/2017 | Bouhnik et al. |
| 2017/0045632 A1 | 2/2017 | Thran |
| 2017/0082759 A1 | 3/2017 | Lyu et al. |
| 2017/0112454 A1 | 4/2017 | Yun et al. |
| 2017/0153338 A1 | 6/2017 | Kovalski et al. |
| 2017/0189720 A1 | 7/2017 | Nozawa et al. |
| 2017/0332025 A1 | 11/2017 | Nozawa et al. |
| 2017/0370499 A1 | 12/2017 | Fujimoto et al. |
| 2018/0059270 A1 | 3/2018 | Hefetz et al. |
| 2018/0110496 A1 | 4/2018 | Levy et al. |
| 2018/0236267 A1 | 8/2018 | Kuang et al. |
| 2018/0358870 A1 | 12/2018 | Kawanami et al. |
| 2020/0163631 A1 | 5/2020 | Okuno |
| 2020/0281546 A1 | 9/2020 | Zilberstien et al. |
| 2020/0289074 A1 | 9/2020 | Zilberstien et al. |
| 2020/0297296 A1 | 9/2020 | Zilberstien et al. |
| 2020/0301033 A1 | 9/2020 | Roth et al. |
| 2021/0093270 A1 | 4/2021 | Zilberstien et al. |
| 2023/0028049 A1 | 1/2023 | Zilberstien |

FOREIGN PATENT DOCUMENTS

| | | |
|---|---|---|
| WO | WO 2019/077542 | 4/2019 |
| WO | WO 2019/077542 A3 | 4/2019 |
| WO | WO 2019/077544 | 4/2019 |
| WO | WO 2019/077548 | 4/2019 |
| WO | WO 2019/077548 A3 | 4/2019 |
| WO | WO 2019/077552 | 4/2019 |

OTHER PUBLICATIONS

Official Action Dated Jul. 7, 2022 from US Patent and Trademark Office Re. U.S. Appl. No. 16/756,520. (58 pages).

Official Action Dated Jan. 30, 2023 from the US Patent and Trademark Office Re. U.S. Appl. No. 16/756,520. (17 pages).

Final Office Action Dated Sep. 20, 2021 from the US Patent and Trademark Office Re. U.S. Appl. No. 16/756,511. (26 pages).

Final Official Action Dated Feb. 23, 2021 From the US Patent and Trademark Office Re. U.S. Appl. No. 16/756,496. (25 Pages).

International Preliminary Report on Patentability Dated Apr. 30, 2020 From the International Bureau of WIPO Re. Application No. PCT/IB2018/058094. (7 Pages).

International Preliminary Report on Patentability Dated Apr. 30, 2020 From the International Bureau of WIPO Re. Application No. PCT/IB2018/058097. (6 Pages).

International Preliminary Report on Patentability Dated Apr. 30, 2020 From the International Bureau of WIPO Re. Application No. PCT/IB2018/058102. (8 Pages).

International Preliminary Report on Patentability Dated Apr. 30, 2020 From the International Bureau of WIPO Re. Application No. PCT/IB2018/058108. (10 Pages).

International Search Report and the Written Opinion Dated Apr. 23, 2019 From the International Searching Authority Re. Application No. PCT/IB2018/058108. (20 Pages).

International Search Report and the Written Opinion Dated Apr. 24, 2019 From the International Searching Authority Re. Application No. PCT/IB2018/058094. (15 Pages).

International Search Report and the Written Opinion Dated Apr. 24, 2019 From the International Searching Authority Re. Application No. PCT/IB2018/058102. (16 Pages).

International Search Report and the Written Opinion Dated Feb. 25, 2019 From the International Searching Authority Re. Application No. PCT/IB2018/058097. (12 Pages).

Interview Summary Dated Mar. 19, 2021 From the US Patent and Trademark Office Re. U.S. Appl. No. 16/756,496. (2 Pages).

Invitation to Pay Additional Fees Dated Feb. 7, 2019 From the International Searching Authority Re. Application No. PCT/IB2018/058094. (2 Pages).

(56) References Cited

OTHER PUBLICATIONS

Invitation to Pay Additional Fees Dated Feb. 7, 2019 From the International Searching Authority Re. Application No. PCT/IB2018/058102. (3 Pages).
Invitation to Pay Additional Fees Dated Feb. 7, 2019 From the International Searching Authority Re. Application No. PCT/IB2018/058108. (2 Pages).
Notice of Allowance Dated Aug. 12, 2020 from the US Patent and Trademark Office Re. U.S. Appl. No. 16/756,492. (9 pages).
Notice of Allowance Dated Oct. 15, 2021 from US Patent and Trademark Office Re. U.S. Appl. No. 16/756,496. (11 pages).
Notice of Allowance Dated Jan. 21, 2022 together eoth Interview Summary Dated Jan. 6, 2022 from US Patent and Trademark Office Re. U.S. Appl. No. 16/756,511. (8 pages).
Official Action Dated Jul. 7, 2021 from the US Patent and Trademark Office Re. U.S. Appl. No. 16/756,496. (12 pages).
Official Action Dated Jun. 10, 2021 From the US Patent and Trademark Office Re. U.S. Appl. No. 16/756,511. (31 Pages).
Official Action Dated Feb. 14, 2022 from US Patent and Trademark Office Re. U.S. Appl. No. 17/120,394. (32 pages).
Official Action Dated Sep. 9, 2020 from the US Patent and Trademark Office Re. U.S. Appl. No. 16/756,496. (27 pages).
Restriction Official Action Dated Apr. 2, 2021 From the US Patent and Trademark Office Re. U.S. Appl. No. 16/756,511. (6 Pages).
Supplementary European Search Report and the European Search Opinion Dated Jun. 4, 2021 From the European Patent Office Re. Application No. 18868897.2. (7 Pages).
Supplementary European Search Report and the European Search Opinion Dated Jun. 9, 2021 From the European Patent Office Re. Application No. 18868387.4. (7 Pages).
Supplementary European Search Report and the European Search Opinion Dated Jul. 14, 2021 From the European Patent Office Re. Application No. 18869177.8. (8 Pages).
Supplementary European Search Report and the European Search Opinion Dated Jun. 21, 2021 From the European Patent Office Re. Application No. 18869300.6. (8 Pages).
Almeida Silva Salvado "Evaluation of the D-SPECT System: Geometry Considerations and Respiratory Motion", Dissertação Mestrado Integrado em Engenharia Biomédica e Biofísica, Perfil de Radiações em Diagnóstico e Terapia [Dissertation Integrated Master in Biomedical Engineering and Biophysics, Radiation Profile in Diagnosis and Therapy], Universidade de Lisboa, Portugal, Faculdade de Ciências Departamento de Física, 134 P., 2012.
Barrento Da Costa "Evaluation of the D-SPECT System: Region Centric Acquisition and Tracer Kinetics", Dissertação Mestrado Integrado em Engenharia Biomédica e Biofísica [Dissertation Integrated Master in Biomedical Engineering and Biophysics], Universidade de Lisboa, Portugal, Faculdade de Ciências, Departamento de Física, 97 P., 2012.
Erlandsson et al. "Assessing Possible Use of CZT Technology for Application to Brain SPECT", 2011 IEEE Nuclear Science Symposium Conference Record, Valencia, Spain, Oct. 23-29, 2011, p. 3354-3358, Oct. 23, 2011.
Gambhir ct al. "A Novel High-Sensitivity Rapid-Acquisition Single-Photon Cardiac Imaging Camera", The Journal of Nuclear Medicine, 50(4): 635-643, Apr. 2009.
Moore et al. "Improved Performance From Modifications to Multidetector SPECT Brain Scanner", The Journal of Nuclear Medicine, 25(6): 688-691, Jun. 1984.
Slomka et al. "Advances in Technical Aspects of Myocardial Perfusion SPECT Imaging", Journal of Nuclear Cardiology, 16(2): 255-276, Published Online Feb. 26, 2009.
Official Action Dated Jul. 17, 2023 from US Patent and Trademark Office Re. U.S. Appl. No. 16/756,520. (15 pages).
Communication Pursuant to Article 94(3) EPC Dated Sep. 21, 2023 From the European Patent Office Re. Application No. 18869300.6 (6 Pages).
Notice of Allowance Dated Oct. 4, 2023 together with Interview Summary Dated Sep. 26, 2023 from the US Patent and Trademark Office Re. U.S. Appl. No. 16/756,520. (12 pages).
Official Action Dated Feb. 1, 2024 from the US Patent and Trademark Office Re. U.S. Appl. No. 17/958,496. (30 pages).
Invitation Pursuant to Rule 137(4) EPC and Article 94(3) EPC Dated Apr. 16, 2024 From the European Patent Office Re. Application No. 18869177.8 (3 Pages).
Communication Pursuant to Article 94(3) EPC Dated Jun. 25, 2024 From the European Patent Office Re. Application No. 18868387.4 (4 Pages).

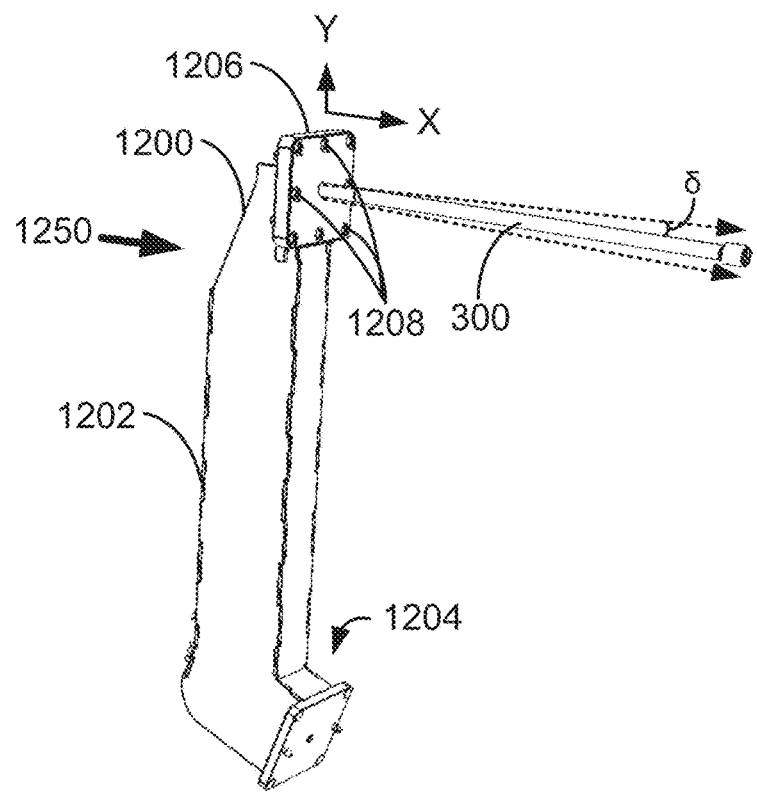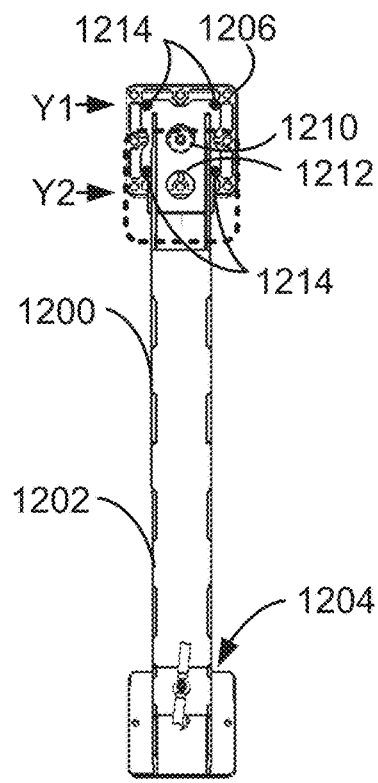
FIG. 12A
FIG. 12B
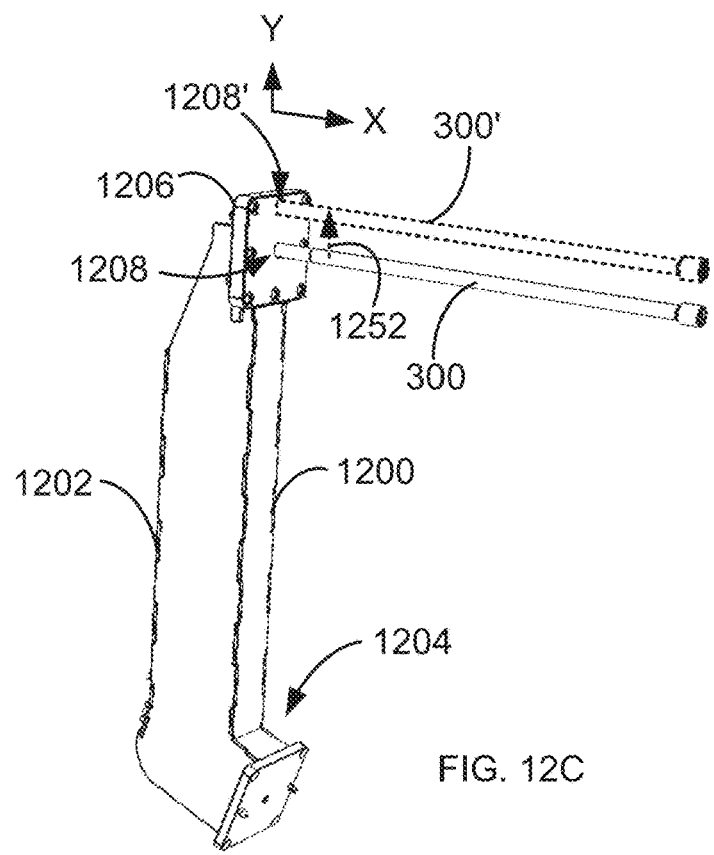
FIG. 12C

CALIBRATION AND QUALITY CONTROL OF A NUCLEAR-MEDICINE (N-M) RADIO IMAGING SYSTEM

RELATED APPLICATIONS

This application is a Continuation of U.S. patent application Ser. No. 16/756,496 filed on Apr. 16, 2020, which is a National Phase of PCT Patent Application No. PCT/IB2018/058108 having International Filing Date of Oct. 18, 2018, which claims the benefit of priority under USC § 119(e) of U.S. Provisional Patent Application No. 62/574,300 filed on Oct. 19, 2017. The contents of the above applications are all incorporated by reference as if fully set forth herein in their entirety.

PCT Patent Application No. PCT/IB2018/058108 is also related to co-filed, co-pending and co-assigned:

International Patent Application No. PCT/IB2018/058102 filed on Oct. 18, 2018 entitled "COOLING OF A NUCLEAR MEDICINE TOMOGRAPHY SYSTEM" which claims the benefit of priority of U.S. Provisional Patent Application No. 62/574,345, filed on Oct. 19, 2017, International Patent Application No. PCT/IB2018/058097 filed on Oct. 18, 2018 entitled "MOVING PARTS IN A NUCLEAR MEDICINE (N-M) IMAGING SYSTEM" which claims the benefit of priority of U.S. Provisional Patent Application No. 62/574,277 filed on Oct. 19, 2017, and International Patent Application No. PCT/IB2018/058094 filed on Oct. 18, 2018 entitled "SAFETY MECHANISMS FOR CLOSE RANGE TOMOGRAPHIC SCANNING MACHINE AND METHODS OF USE" which claims the benefit of priority of U.S. Provisional Patent Application No. 62/574,294 filed on Oct. 19, 2017, the contents of which are all incorporated by reference as if fully set forth herein in their entirety.

PCT Patent Application No. PCT/IB2018/058108 is also related to U.S. Patent Publication Nos. 2015/0119704, 8,338,788, 8,492,725 and 8,748,827 the contents of which are all incorporated by reference as if fully set forth herein in their entirety.

FIELD AND BACKGROUND OF THE INVENTION

The present invention, in some embodiments thereof, relates to Nuclear-Medicine (N-M) Radiotracers Imaging systems and, more particularly, but not exclusively, to calibration and quality control of a NuclearRadio Imaging system.

Nuclear medicine involves application of radioactive substances in the diagnosis and treatment of disease. Nuclear-Radio Imaging devices, e.g., Single Photon Emission Computed Tomography (SPECT) and Positron Emission Tomography (PET) scanners are designed to record radiation emitting from within the body and generate an image corresponding to the recorded emission.

The Nuclear-Radio Imaging systems used in nuclear medicine are complex systems that require quality control programs such as calibration protocols to ensure the integrity of the data obtained from the patient.

SUMMARY OF THE INVENTION

According to an aspect of some embodiments of the present invention there is provided a method for calibrating an N-M imaging system including: providing a plurality of N-M imaging system scanning units, each of the scanning units individually movable in at least two dimensions and positioned at a first position, positioning at least one source of radiation between at least two of the plurality of scanning units, concurrently moving each of the scanning units to a second position at a source acquisition angle, recording a unique movement in 3D space of each of the scanning units from the first position to the second position at the source acquisition angle, and generating for each of all of the scanning units information regarding the positions and path of movement of all of the scanning units based on the recorded unique movements.

According to some embodiments, the at least one source of radiation includes a line source. According to some embodiments, the position includes at least one of orientation and location in 3D space. According to some embodiments, paths of movement from a first position (e.g., at a source acquisition angle) to a second position (e.g., at a source acquisition angle) is unique for every scanning unit. According to some embodiments, paths of movement from a first position (e.g., at a source acquisition angle) to a second position (e.g., at a source acquisition angle) differs between scanning units. According to some embodiments, the at least one source of radiation is positioned at a known location. According to some embodiments, the plurality of scanning units are coupled to a rotor configured to at least partially rotate about a center of rotation (COR).

According to some embodiments, at least one of the plurality of scanning units includes at least one detector array arranged along at least one surface. According to some embodiments, the at least one of the scanning units is configured to pivot about a longitudinal axis (P). According to some embodiments, the at least one of the scanning units is configured to rotate with the rotor about the COR. According to some embodiments, the at least one scanning units is configured to pivot and maintain an orientation in which the at least one detector array is oriented in parallel to radiation effluence from the at least one source of radiation.

According to some embodiments, the scanning unit includes a collimator and the method further includes positioning at least one of the scanning units oriented at an angle (α) at which the collimator blocks all radiation parallel to radiation effluence from the at least one source of radiation, measuring zero (0) signals ($S_{PMT}$) from the at least one detector array, registering signals produced from at least one detector array and measuring scatter radiation at the position, pivoting the scanning unit about the axis (P), sampling the detector exposure at at least one angle (α) of rotation, and generating information regarding detector performance.

According to some embodiments, the detector performance includes at least one of a uniformity map and energy resolution. According to some embodiments, the method further comprises rotating the rotor and pivoting the scanning unit about the axis (P), sampling the detector exposure at at least one second angle (α) of rotation, rotating the rotor and repeating the scanner unit pivoting and sampling of the detector exposure at different positions without moving or readjusting the line source of radiation. According to some embodiments, the method further includes positioning a plurality of sources of radiation among the plurality of scanning units. According to some embodiments, the source of radiation emits radiation at at least two different frequencies.

According to an aspect of some embodiments of the present invention there is provided a method for calibrating an N-M imaging system scanning unit including: providing at least one N-M imaging system scanning unit having a longitudinal axis (P) and at least one detector array arranged along at least one scanning surface, providing at least one line source of radiation, positioning the at least one line source of radiation opposite the scanning surface at a distance from and in parallel to the at least one detector array, pivoting the scanning unit about the axis (P), sampling the detector exposure at at least one angle ($\alpha$) of rotation, and generating information regarding performance of the at least one detector array.

According to some embodiments, the method further includes further obtaining the information and correcting at least one pixel registration signal in accordance with the information, positioning a plurality of line sources of radiation opposite the scanning surface and measuring at least one of unique path of movement, speed of movement, angular movement and rate of movement of the scanning unit in respect to the plurality of line sources.

According to an aspect of some embodiments of the present invention there is provided a method for calibrating an N-M imaging system including: providing a plurality of N-M imaging system scanning units mounted on a rotor, positioning at least one source of radiation within a circumference of the rotor, concurrently moving each of the scanning units to a second position at a source acquisition angle to scan the at least one line source of radiation, recording pre-rotation unique movements in 3D space of each of the scanning units from the recorded first position to the second position at a source acquisition angle, rotating the rotor by at least an angle ($\beta$), concurrently moving each of the scanning units from the second position at a source acquisition angle to a third position at a source acquisition angle to scan the at least one line source of radiation, and generating at least one angular orientation map of all of the scanning units based on the unique movements.

According to some embodiments, the source of radiation includes a line source of radiation. According to some embodiments, the method further includes the method further including recording a first position of each of the scanning units, and recording unique post-rotation movement in 3D space of each of the scanning units from the second position to the third position at a source acquisition angle. According to some embodiments, unique movements of at least two scanning units differ in at least one of direction and speed. According to some embodiments, the pre-rotation movement is different from the post-rotation movement.

According to some embodiments, the method further includes receiving and processing at least movement data regarding the unique movement of one or more scanning units, and providing at least one scanning unit driving motor at least one of a scanning angle and/or movement instruction for one or more specific scanning unit corrected for the received and processed movement data. According to some embodiments, the method further includes updating a factory produced angular orientation map according to the generated angular orientation map. According to some embodiments, the method further includes applying both a factory produced angular orientation map and the generated angular orientation map. According to some embodiments, the method further includes attaching a tracking tag to each of the scanning units, providing an external localization tracker, and tracking and recording a first position of each of the scanning units. According to some embodiments, the method further includes at least one patient table having one or more tracking tags and tracking movement of the patient table in 3D space.

According to an aspect of some embodiments of the present invention there is provided a method for calibrating an N-M imaging system including: providing a plurality of N-M imaging system scanning units each mounted on at least one extending arm, providing at least one line source of radiation between the scanning units, extending at least one of the extending arms from a reference location position to a second position along a first distance (L1), concurrently moving the scanning units to face the at least one line source of radiation, recording a unique movement in 3D space of each of the scanning units from the reference location position to the second position, and generating at least one angular orientation map of all of the scanning units based on the recorded unique movements. According to some embodiments, the reference location includes a "Home" location.

According to some embodiments, the method further includes further extending at least one of the extending arms to a third position along a distance (L2) from the "Home" position, concurrently moving the scanning units to face the at least one line source of radiation, recording a unique movement in 3D space of each of the scanning units from the second position to the third position, and generating a second angular orientation map of all of the scanning units based on the recorded unique movements.

According to an aspect of some embodiments of the present invention there is provided a line source holding jig for calibrating an N-M imaging system: at least one arm having a coupling at a first end configured to couple the jig to a stationary portion of an N-M imaging system, and at least one line source holder plate at a second end opposite to the first end, the line source holder plate including at least one line source positioning bore sized to receive an end of at least one line source.

According to some embodiments, the holder plate is adjustable. According to some embodiments, the holder plate includes at least one adjusting screw configured to adjust a tilt angle ($\delta$) of a long axis of a line source in reference to a predetermined X-axis. According to some embodiments, the holder plate is configured to adjust the line source along a Y-axis. According to some embodiments, the jig holder plate is configured to hold a plurality of line sources. According to some embodiments, the jig holder is configured to hold any number of line sources between 1 and 10. According to some embodiments, the jig holder is configured to hold a plurality of line sources at least two having different wavelengths.

According to an aspect of some embodiments of the present invention there is provided a method for calibrating an N-M imaging system comprising: providing a plurality of N-M imaging system scanning units, each of said scanning units individually movable in at least two dimensions and each scanning unit positioned at an individual scanning unit first position; positioning at least one source of radiation between at least two of said plurality of scanning units; moving each of said scanning units to an individual scanning unit second position, where each scanning unit is orientated at an individual scanning unit source acquisition angle;

recording movement in 3D space of each of said scanning units; and generating, for each of all of said scanning units, information regarding said positions and path of movement of all of said scanning units, based on said recorded movements.

According to some embodiments, said moving comprises concurrently moving said scanning units. According to some embodiments, said recording comprises receiving and recording encoder data. According to some embodiments, each said scanning unit includes one or more associated encoder configured to measure movement of said scanning unit, and wherein said recording comprises receiving, for each said scanning unit, encoder data from said one or more associated encoder and recording said encoder data. According to some embodiments, said generating comprises receiving scanning unit sensor data. According to some embodiments, said moving comprises one or more of: rotating a rotor about a center of rotation (COR), to which said scanning units are coupled; and axially moving one or more of said scanning units with respect to said COR.

According to some embodiments, said at least one source of radiation comprises a line source. According to some embodiments, said position comprises at least one of orientation and location in 3D space. According to some embodiments, said at least one source of radiation is positioned at a known location. According to some embodiments, said plurality of scanning units are coupled to a rotor configured to at least partially rotate about a center of rotation (COR). According to some embodiments, at least one of said plurality of scanning units comprises at least one detector array arranged along at least one surface. According to some embodiments, said generating comprises receiving pixel signals from said at least one detector array. According to some embodiments, each said scanning unit comprises a detector array; and wherein said generating comprises receiving pixel signals from one or more of said detector arrays. According to some embodiments, said at least one of said scanning units is configured to pivot about a longitudinal axis (P).

According to some embodiments, said at least one scanning units is configured to pivot and maintain an orientation in which said at least one detector array is oriented in parallel to radiation effluence from said at least one source of radiation. According to some embodiments, said scanning unit comprises a collimator and said method comprises: positioning at least one of said scanning units oriented at an angle (a) at which said collimator blocks all radiation parallel to radiation effluence from said at least one source of radiation; measuring zero (0) signals ($S_{PMT}$) from said at least one detector array. According to some embodiments, said method further comprises registering signals produced from at least one detector array and measuring scatter radiation at said position. According to some embodiments, said generating comprises: pivoting said scanning unit about said axis (P); sampling exposure of said detector array at at least one pivot angle ($\alpha$); and generating information regarding detector performance. According to some embodiments, said detector performance comprises at least one of a uniformity map and energy resolution. According to some embodiments, said moving comprises rotating said rotor; wherein said generating comprises: pivoting at least one of said scanning units about a longitudinal axis (P); and sampling detector exposure at at least one second angle ($\alpha$) of rotation. According to some embodiments, said moving comprises repeating said rotating of said rotor; and wherein said generating comprises: repeating said scanner unit pivoting and said sampling of said detector exposure at different positions without moving or readjusting said source of radiation. According to some embodiments, said positioning comprises positioning a plurality of sources of radiation among said plurality of scanning units. According to some embodiments, said plurality of sources of radiation emit radiation at at least two different frequencies.

According to an aspect of some embodiments of the present invention there is provided method for calibrating an N-M imaging system scanning unit comprising: providing at least one N-M imaging system scanning unit having a longitudinal axis (P) and at least one detector array arranged along at least one scanning surface; providing at least one line source of radiation; positioning said at least one line source of radiation opposite said scanning surface at a distance from and in parallel to said at least one detector array; pivoting, through a range of angles ($\alpha$) of rotation, said scanning unit about said axis (P); sampling said detector exposure at at least one angle ($\alpha$) of rotation; and generating, based on said sampling, information regarding performance of said at least one detector array.

According to some embodiments, the method comprises correcting at least one pixel registration signal in accordance with said information. According to some embodiments, positioning comprises positioning a plurality of line sources of radiation opposite said scanning surface. According to some embodiments, said generating comprises measuring at least one of: unique path of movement, speed of movement, angular movement and rate of movement of said scanning unit in respect to said plurality of line sources.

According to an aspect of some embodiments of the present invention there is provided method for calibrating an N-M imaging system comprising: providing a plurality of N-M imaging system scanning units mounted on a rotor, each said scanning unit positioned at an individual scanning unit first position; positioning at least one source of radiation within a circumference of said rotor; moving each of said scanning units to an individual scanning unit second position, where each scanning unit is orientated at an individual scanning unit source acquisition angle to scan said at least one source of radiation; recording pre-rotation movement in 3D space of each of said scanning units from said first position to said second position; rotating said rotor by at least an angle ($\beta$); concurrently moving each of said scanning units from said individual scanning unit second position at an individual scanning unit source acquisition angle to an individual scanning unit third position at an individual scanning unit source acquisition angle, to scan said at least one source of radiation; and generating at least one angular orientation map of all of said scanning units based on said movements.

According to some embodiments, said source of radiation comprises a line source of radiation. According to some embodiments, said method further comprising: recording a first position of each of said scanning units; and recording unique post-rotation movement in 3D space of each of said scanning units from said second position to said third position at a source acquisition angle. According to some embodiments, unique movements of at least two scanning units differ in at least one of direction and speed. According to some embodiments, pre-rotation movement is different than said post-rotation movement.

According to some embodiments, said method comprises: receiving and processing movement data regarding said movement of one or more scanning units; and generating at least one of a scanning angle and a movement instruction for one or more specific scanning unit corrected for said received and processed movement data.

According to some embodiments, said method comprises updating a factory produced angular orientation map according to said generated angular orientation map.

According to some embodiments, said method comprises applying both a factory produced angular orientation map and said generated angular orientation map.

According to some embodiments, said method comprises: attaching a tracking tag to each of said scanning units; providing an external localization tracker; and tracking and recording a first position of each of said scanning units. According to some embodiments, said method comprises: providing at least one patient table having one or more tracking tags. According to some embodiments, said method comprises: tracking movement of said patient table in 3D space.

According to an aspect of some embodiments of the present invention there is provided method for calibrating an N-M imaging system comprising: providing a plurality of N-M imaging system scanning units each mounted on at least one extending arm; providing at least one line source of radiation between said scanning units; extending at least one of said extending arms from a reference location position to a second position along a first distance (L1);
  concurrently moving said scanning units to face said at least one line source of radiation;
  recording a unique movement in 3D space of each of said scanning units from said reference location position to said second position; and generating at least one angular orientation map of all of said scanning units based on said recorded unique movements.

According to some embodiments, said concurrently moving comprises pivoting said scanning units, each about a scanning unit axis. According to some embodiments, said scanning unit axis is parallel to an axis of said at least one line source. According to some embodiments, said reference location comprises a "Home" location.

According to some embodiments, said method comprises: extending at least one of said extending arms to a third position along a distance (L2) from said reference location position; concurrently moving said scanning units to face said at least one line source of radiation; recording a second unique movement in 3D space of each of said scanning units from said second position to said third position; and generating a second angular orientation map of all of said scanning units based on said recorded second unique movements.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof.

Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 12A, 12B, 12C and 12D are perspective and plan view simplified illustrations of a line source jig in accordance with some embodiments of the invention.

DESCRIPTION OF SPECIFIC EMBODIMENTS OF THE INVENTION

Figure 1:
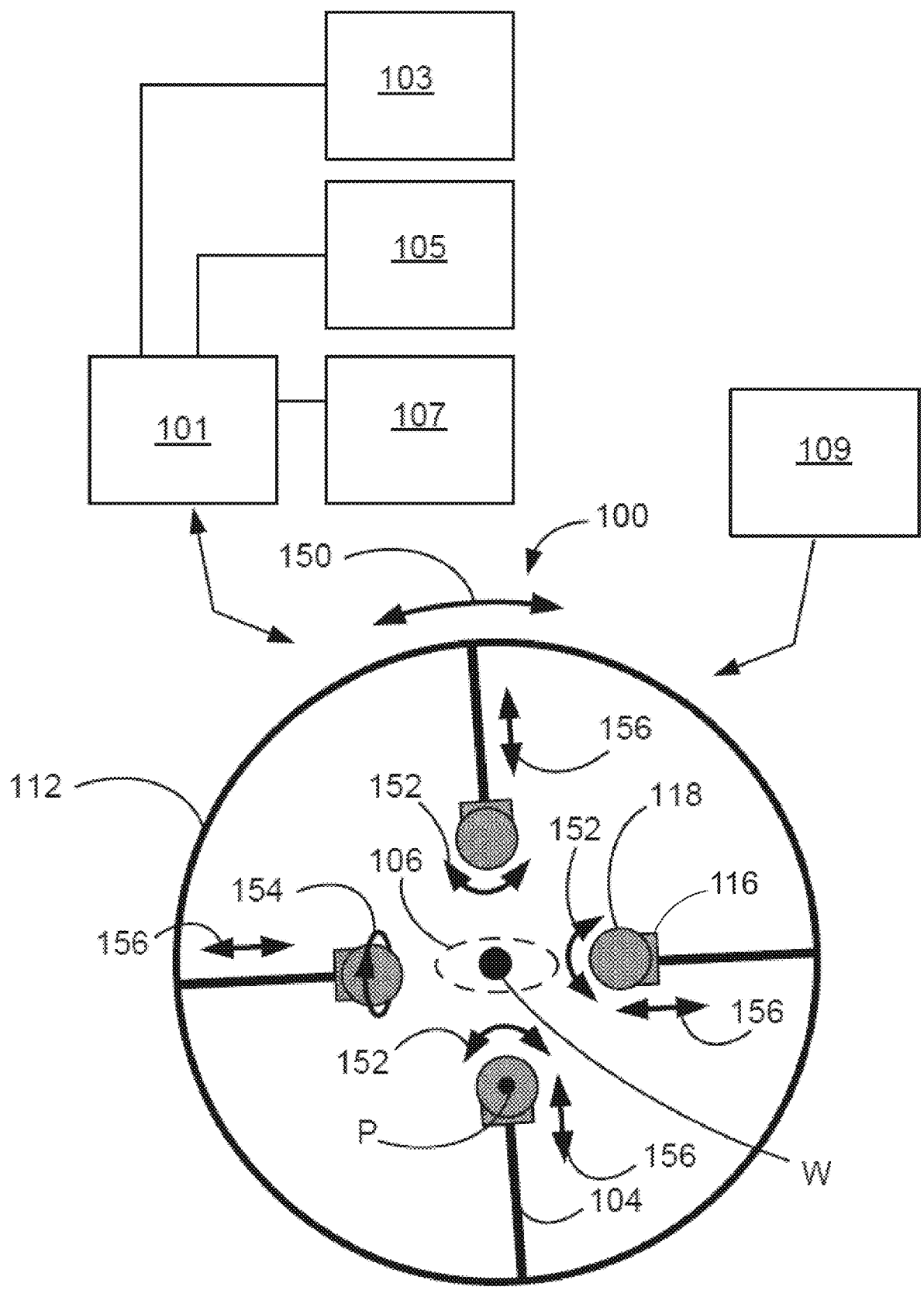
FIG. 1 is a diagram and plan view simplified illustration of a Nuclear Medicine (N-M) imaging system in accordance with some embodiments of the invention.

The present invention, in some embodiments thereof, relates to Nuclear-Medicine Imaging systems and, more particularly, but not exclusively, to calibration of a Nuclear-Medicine Imaging system.

Overview

A broad aspect of some embodiments of the invention relates to calibration of a NM imaging system including a plurality of scanning units, by collecting radiation measurements of a source using the scanning units.

In some embodiments, measurements are collected during movement of the scanning units with respect to the source. Where, in some embodiments, movement includes one or more of; changing an angle of scanning unit/s with respect to the source, rotating scanning unit/s about an axis (e.g. central axis) of the NM imaging system and/or a location of the source, linearly translating scanning unit/s towards and/or away an axis of the NM imaging system and/or a location of the source.

In some embodiments, the NM system includes a rotor (e.g. gantry) onto which the plurality of scanning units are mounted, where rotation of the rotor rotates the scanning units. Where, in some embodiments, the scanning units are extendable (and/or retractable) e.g. linearly extendable and/or extendable towards a center of the rotor. In some embodiments, scanning units are rotatable e.g. about one or more axis e.g. with respect to the rotor and/or extendable arm. In an exemplary embodiment, a center of rotation of the NM system (e.g. of the rotor of the system) is parallel to an axis of rotation (P) of the scanning units. In some embodiments, a detector array of a scanning unit is elongate and an axis of rotation of the scanning unit (P) is a longitudinal axis of the detector array and/or scanning unit.

An aspect of some embodiments of the invention relates to calibrating and/or assessing performance of scanning unit detectors of a NM imaging system.

According to an aspect of some embodiments of the present invention there is provided a method for calibrating (e.g. scanning detectors) one of a N-M imaging system and/or generating information regarding detector performance e.g., a scanning detector uniformity map and/or energy resolution calibration.

In some embodiments, during imaging (e.g. of tissue) by the NM imaging system, generated information regarding detector performance is used to correct detector radiation measurement signal/s e.g. prior to and/or during reconstruction of images from radiation measurement data.

In some embodiments, a detector is rotated about one or more an axis with respect to a radiation source and detector measurements are collected at different rotation angles. In some embodiments, the detector is rotated about a single axis e.g. pivot axis P. In some embodiments, the source is a line source orientated parallel to the pivot axis. In some embodiments, measurements are collected for a plurality of detectors e.g. for all of a plurality of scanning detectors of the system, e.g. simultaneously e.g. using a single line source.

According to some embodiments, the method comprises providing at least one N-M imaging system scanning unit having a longitudinal axis (P) and at least one array of detector modules arranged along at least one scanning surface. According to some embodiments, the method includes providing at least one line source of radiation and positioning the at least one line source of radiation opposite the scanning surface at a distance from and in parallel to said at least one detector array.

According to some embodiments, pivoting said scanning unit about said axis (P) exposes different regions at different levels of the detector array to effluence from the line source. According to some embodiments, the units include a collimator. According to some embodiments, the differences in level of effluence depend on angle of impingement of the effluence on the collimator and/or detector modules. According to some embodiments, the method includes sampling the detector exposure at at least one angle ($\alpha$) of rotation and generating information regarding detector performance e.g., a uniformity map of said at least one detector array.

A broad aspect of some embodiments of the invention relates to moving scanning units with respect to a source (e.g. from a first position to a second position, for each scanning unit) and pivoting one or more scanning unit (e.g. each scanning unit) so that a scanning surface of the scanning unit faces the source.

In some embodiments, control signal/s to actuator/s pivoting the scanning unit to face the source (e.g. for each scanning unit) are based on one or more of: A known positon of the source e.g. within the circumference of the rotor. An estimated position of the scanning unit e.g. estimated from a start position and/or position measurement data for the scanning unit (e.g. provided by one or more encoder). Radiation measurements collected by the scanning unit, for example, in some embodiments, the scanning unit radiation measurements are used as feedback for generating the actuator control system. For example, in some embodiments, peak radiation measurements on a scanning unit detector surface are identified with respect to position on the detector surface, and feedback is generated to move (e.g. pivot) the detector surface until the peak radiation is measured at a central region of the detector surface.

In some embodiments, movement includes rotation of the gantry.

In some embodiments, movement includes extending (and/or retracting) scanning unit/s with respect to a source.

In some embodiments, the pivoting is performed concurrently with the rotational and/or extension/retraction movement of the scanning unit/s.

In some embodiments, scanning unit measurement/s are collected during and/or between movements e.g. for each scanning unit. In some embodiments, the measurement/s are used to correct movement and/or position commands e.g. for each scanning unit.

In some embodiments, measurement of mechanical movements of the scanning units during calibration methods (e.g. as described within this document) are compared with scanning unit position as estimated from scanning unit detector radiation measurements of one or more source. In some embodiments, detected inaccuracy of positioning of the scanning unit/s is used to correct position and/or orientation control signals (e.g. sent to actuator/s) to the scanning unit/s during scanning of tissue.

According to an aspect of some embodiments of the present invention there is provided a method for calibrating at least one N-M imaging system and generating a scanning unit angular orientation map. According to some embodiments, the system comprises a controller.

According to some embodiments, the system learns a movement and orientation unique to each and every scanning unit from a first position to a second position at a source acquisition angle. According to some embodiments, the controller is configured to use the learned information to correct moving and positioning orders specific and unique to each and every scanning unit in accordance with the learned information. According to some embodiments, the method comprises providing a plurality of N-M imaging system scanning units mounted on a rotor and recording a first position of each of the scanning units. The terms "Position" and "Positioning" as relating to scanning units 118 and used herein mean at least one of an orientation and location in 3D space of the scanning unit.

According to some embodiments, the method includes positioning at least one source of radiation (e.g. a line source of radiation) within a circumference of the rotor and concurrently moving each of the scanning units to a second position at a source acquisition angle to scan the line source of radiation.

According to some embodiments, the method further comprises recording pre-rotation (e.g. of a rotor) unique movements in 3D space of each of the scanning units from the recorded first position to the second position at a source acquisition angle. Rotating the rotor by at least an angle ($\beta$) then concurrently moving each of the scanning units from the second position at a source acquisition angle to a third position at a source acquisition angle to scan the line source of radiation.

According to some embodiments, the method further comprises concurrently moving each of the scanning units from the second position at a source acquisition angle to a third position at a source acquisition angle during the rotation of the rotor.

According to some embodiments, recording unique post-rotation movement in 3D space of each of the scanning units from the second position to the third position at a source acquisition angle and generating at least one angular orientation map of all of the scanning units based on the recorded unique movements. According to some embodiments, unique movements of at least two scanning units differ in at least one of direction and speed.

According to some embodiments, the method further comprises learning an angular orientation of one or more scanning units and providing at least one scanning unit driving motor a unique scanning angle and/or movement instruction corrected for the learned angular orientation of one or more specific scanning unit based on the generated angular orientation map.

According to some embodiments, the method further comprises comparing the generated angular orientation map with a factory produced angular orientation map and updating the factory produced angular orientation map accordingly.

According to some embodiments, the method further comprises assessing the one or more scanning units angular orientation inaccuracies and correcting for assessed inaccuracies.

According to an aspect of some embodiments of the present invention there is provided a method for calibrating at least one N-M imaging system correcting for assessed inaccuracies.

According to some embodiments, the method comprises providing a plurality of N-M imaging system scanning units each mounted on at least one extending arm and positioning a line source of radiation between the scanning units.

In some embodiments, position of the scanning units is changed, where radiation measurements of the scanning units are measured in two or more positions. For example, in some embodiments, the method includes extending at least one of the extending the arms from a "Home" position to a second position along a first distance (L1). In some embodiments, after movement to the second position, the scanning unit/s are moved (e.g. after movement from a first position to a second position or concurrently to movement between positions) to scan or face the at least one line source of radiation. According to some embodiments, moving the scanning units to scan or face the at least one line source of radiation is performed concurrently and/or during extending the arms from a "Home" position to a second position along a first distance (L1).

According to some embodiments, the method further includes recording a unique movement in 3D space of each of the scanning units from the "Home" position to the second position and generating at least one angular orientation map of all of the scanning units based on the recorded unique movements.

According to some embodiments, the method further includes further extending at least one of said extending arms to a third position along a distance (L2) from "Home" position then concurrently moving said scanning units to scan or face the at least one line source of radiation. According to some embodiments, this is followed by recording a unique movement in 3D space of each of the scanning units from the second position to the third position and generating a second angular orientation map of all of the scanning units based on the recorded unique movements.

According to an aspect of some embodiments of the present invention there is provided a jig for holding a line source during a calibration process of an N-M imaging system. According to some embodiments, the jig comprises at least one arm having a coupling at a first end configured to couple the jig to a stationary portion of an N-M imaging system and at least one line source holder plate at a second end opposite to the first end, including at least one line source positioning bore sized to receive an end of at least one line source.

According to some embodiments, the jig holder plate is adjustable and comprises at least one adjusting screw. According to some embodiments, the adjusting screw is configured to adjust a tilt angle (δ) of a long axis of a line source in reference to a predetermined X-axis. According to some embodiments, the holder plate is configured to adjust said line source along a Y-axis. According to some embodiments, the jig holder plate is configured to hold a plurality of line sources at least two having different wavelengths.

In some embodiments, the NM system is a modular system where, in some embodiments, the system includes a variable number of scanning units. For example, in some embodiments, a scanning unit is physically added or removed from the system. For example, in some embodiments, less than all of the scanning units are used (e.g. in the case of malfunction), in which case, in some embodiments, calibration includes movements and measurements (e.g. as described within this document) for the scanning units in use.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

General

As used herein, the terms "Circumferentially" refers to arrangement of one or more N-M imaging system components in a circular pattern (e.g., scanning units on a rotor or gamma ray detector arrays on a scanning unit) and having a common central axis of rotation. Likewise, "Circumferential Movement" or "Circumferential Direction of Movement" refers to movement of one or more of the N-M imaging system components in respect to the common central axis of rotation. As used herein, the terms "Axial" or "Axially" refer to positioning or direction of movement along a common central axis of rotation of N-M imaging system components arranged in a circular pattern.

Referring now to the drawings, FIG. 1 is a simplified diagram illustration of a Nuclear Medicine (N-M) imaging system described in detail in US Patent Application Publication No. 2015/0119704 the contents which is incorporated by reference as if fully set forth herein in their entirety. In some embodiments, N-M imaging system 100 communicates with a controller 101 and via controller 101 with one or more monitors 103, one or more input systems 105, e.g., a touch screen or keypad and a patient table 107. N-M imaging system 100 also comprises or is connected to one or more sources of electrical power 109.

FIG. 1, illustrates an N-M imaging system 100 rotor 112 and one or more scanning units or cameras 118 mounted on one or more extendable arms 104 coupled to rotor 112. In some embodiments, N-M imaging system 100 rotor 112 comprises between 1-20, 2-16, 4-14 or more than 14 scanning units. In some embodiments, N-M imaging system 100 rotor 112 comprises 12 scanning units. All other N-M imaging system 100 components have been removed for purposes of simplicity of explanation.

In some embodiments, N-M imaging system 100 comprises one or more moveable components (e.g., rotor 112, extending arms 104, moveable scanning units 118) to enable a complete scan of all parts of a body to be examined. Movement of scanning units 118 comprises pendulous (e.g., arrow 152), axial and/or reciprocal (arrow 156) and rotational in various planes (arrows 150 and 154) and angular movement.

In some embodiments, and e.g. as explained in greater detail elsewhere herein, the sum-total of N-M imaging system 100 one or more moveable components brings one or more scanning units 118 to be moveable along one or more planes in 3D space. In some embodiments, one or more scanning units 118 have 4 degrees of freedom of movement. In some embodiments, one or more scanning units 118 have 6 degrees of freedom of movement.

In some embodiments, all scanning units 118 move in the same direction and in the same speed. Alternatively and optionally, one or more scanning units 118 move in different directions and/or in different speeds in respect to each other and/or in respect to gantry rotor 112.

As shown in the exemplary embodiment shown in FIG. 1 and indicated by a double headed arrow 150, N-M imaging system 100 rotor 112 is configured, in some embodiments, to rotate back-and-forth about a central axis (W) oriented perpendicular to a plane defined by the rotor, which in FIG. 1 corresponds to the plane of the paper. In some embodiments, axis (W) corresponds to a longitudinal axis of a person 106 being examined and marked in FIG. 1 by a broken line.

In some embodiments, and as indicated by a double headed arrow 152, one or more scanning units 118 are configured to pivot along an axis of rotation that coincides with scanning units 118 longitudinal axis (P). In some embodiments, longitudinal axis (P) is oriented in parallel to rotor 112 axis of rotation (W), however, in some embodiments and optionally, scanning units 118 are configured to be positioned at an angle in respect to rotor central axis (W) by at least partially rotating about extendable arms 104 as indicated arrow 154.

In some embodiments, and as shown in the exemplary embodiment shown in FIG. 1, extendable arms 104 are configured to extend and retract radially inward and outward, translating scanning units 118 radially inward and outward as indicated by double headed arrow 156.

All movements of rotor 112, scanning units 118 and extendable arms 104 can be done separately or concurrently and involve activation of complex mechanical movement mechanisms. Every movement mechanism includes one or more dedicated movement encoders (not shown) that communicate the location and/or spatial orientation of a system component (e.g., scanning unit 118, extending arm 104, gantry rotor 112 and patient table). The movement mechanisms include one or more of at least a rotor 112 rotating mechanism, an extending arm 104 axial movement encoder, a scanning unit 118 pivot encoder and patient table 906 X-axis movement encoder, Y-axis movement encoder and Z-axis movement encoder.

As in many mechanical systems, maladjustment of the mechanical components may occur and/or accumulate over time bringing about "drifting" of one or more components from their original or predetermined spatial position. System uniformity is most sensitive to changes in N-M imaging system performance and calibration is essential to minimize the effect of the various above described optional changes in the spatial position and orientation of scanning units 118 in respect to an object being scanned.

In some embodiments, calibration of the N-M imaging system includes at least three components:

a) Generation of information regarding detector performance e.g., a scanning detector uniformity map and energy resolution calibration.
b) Calibration of detector spatial orientation.
c) Structural or mechanical calibration.

Exemplary Scanner Detector Uniformity Map and Energy Resolution Calibration

Figures 2A, 2B:
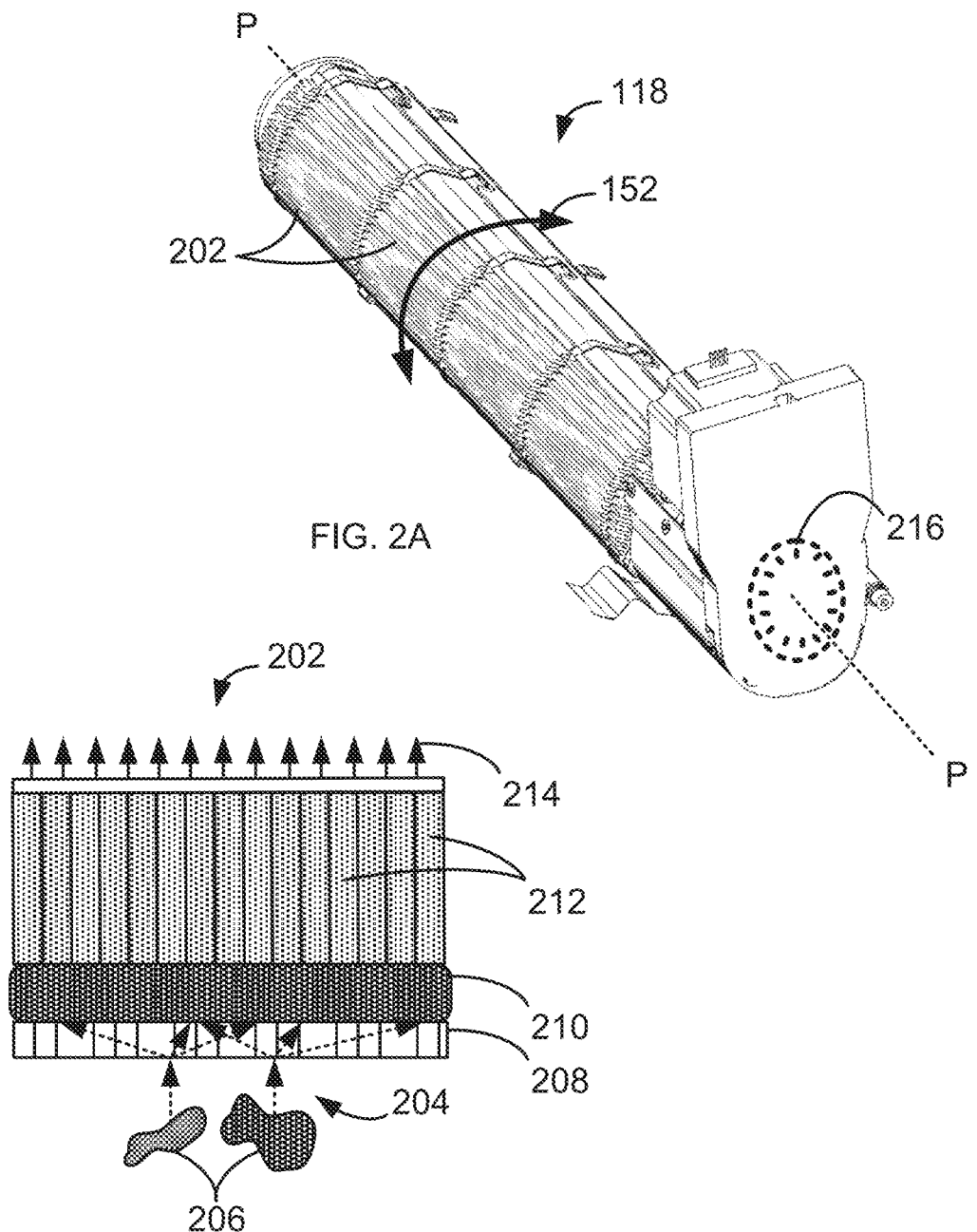
FIGS. 2A and 2B are a diagram and perspective view simplified illustrations of a N-M imaging system scanning unit in accordance with some embodiments of the invention.

Reference is now made to FIGS. 2A and 2B, which are a diagram and perspective view simplified illustrations of a N-M imaging system scanning unit in accordance with some embodiments of the invention. In the exemplary embodiment depicted in FIG. 2A a scanning unit 118 comprises one or more detector 212 arrays 202 oriented axially along at least one surface of scanning unit 118. Detector arrays 202 are circumferentially moveable upon pivotal rotation of scanning unit 118 about longitudinal axis (P) as indicated by a double headed arrow 152. In some embodiments, scanning unit 118 comprises an encoder 216 in communication with controller 101 and provides controller 101 with information regarding an angle (e.g. pivot angle) of rotation ($\alpha$) of scanning unit 118 in respect to a predetermined reference e.g., extendable arms 104 coupled to rotor 112.

FIG. 2B is a simplified diagram of an exemplary embodiment of a detector array 202 designed to detect radiation (e.g. gamma radiation) 204 emitted from one or more scanned bodies 206. In some embodiments, detector arrays 202 optionally comprise gas detectors, scintillators and/or semiconductors.

In some embodiments, detector array 202 comprises one or more collimators or grids 208, one or more Sodium Iodide (NaI) crystals 210, one or more Photomultiplier Tubes (PMT) 212 or modules and circuitry 214 including, for example, one or more position logic circuits, a pulse height analyzer (PHA) and digital correction circuitry. In some embodiments, detectors 212 of array 202 comprise Cadmium Zinc Telluride (CZT) detectors.

For calibrating detectors performance e.g. uniformity maps or performing detector QC without dismantling the collimator, the common technic is to expose a detector to a uniform radiation using a flood source (flat source). The flood source can be a solid isotope such as cobalt-57 sheet or a fillable flat container filled with liquid isotope such as Technetium 99m.

However, as described elsewhere herein, in some embodiments, scanning unit 118 comprises a plurality of detectors arranged in arrays. Obtaining simultaneously uniform radiation over all of the detectors may in some cases be challenging in light of the size and arrangement of the detectors, moreover when the detector arrays 202 comprise collimators as well. In some circumstances a plurality of flood sources are used but this solution may be not practical for the disclosed N-M imaging system scanning unit.

Reference is now made to FIGS. 3A, 3B, 3C, 3D and 3E, which are perspective view and side view simplified illustrations of a scanning unit calibration setup in accordance with some embodiments of the invention. As shown in the exemplary embodiment depicted in FIG. 3A, a line radiation source 300 is placed at a distance from scanning unit 118 oriented axially parallel to longitudinal axis P of scanning unit 118. In some embodiments, line radiation source 300 comprises line, a plurality of points arranged in a linear pattern or a cylinder source filled with liquid isotope (e.g., Tc-99m) or made from a solid isotope (e.g., Co57).

Figure 3A:
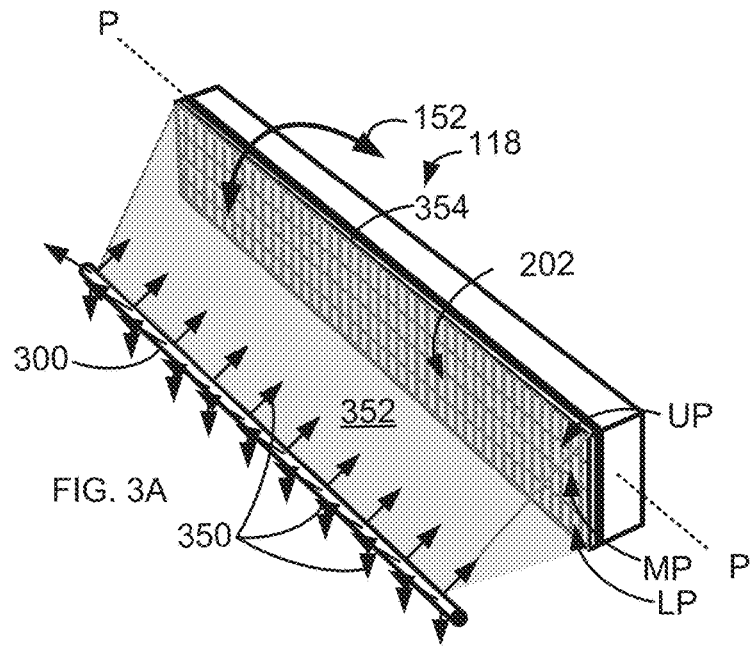
FIGS. 3A, 3B, 3C, 3D and 3E are perspective view and side view simplified illustrations of a scanning unit calibration setup in accordance with some embodiments of the invention.

In some embodiments, line radiation source 300 emits isotropic radiation (having uniform intensity of radiation in all directions) depicted in FIG. 3A by arrows 350. A potential advantage of using a line source of isotropic radiation is in that all modules arrays of one or more scanning unit 118 can be calibrated at once as will be explained in greater detail elsewhere herein. A potential advantage of using a line source of isotropic radiation is in that dimensions of an area irradiated by a flood or spot source is limited whereas line or rod radiation sources have greater areas of coverage, having at least a longitudinal dimension (e.g., between 75 mm and 130 mm), about 2-3 times the longitudinal dimension of flood or spot sources. In some embodiments, a single line or rod source emits radiation effluence, schematically illustrated in FIG. 3A by a shaded area 352, sufficient for calibration of one or more scanning units 118. In some embodiments, line source 300 emits radiation having one or more frequencies.

Though line radiation source 300 emits radiation in all directions –360 degrees about its longitudinal axis—for purposes of simplifying the explanation, shaded area 352 in FIGS. 3A-3E depict effluence of radiation from source 300 that is limited to coverage of scanning unit 118 detector arrays 202 and radiation emitted in other directions is currently ignored.

Figure 3B:
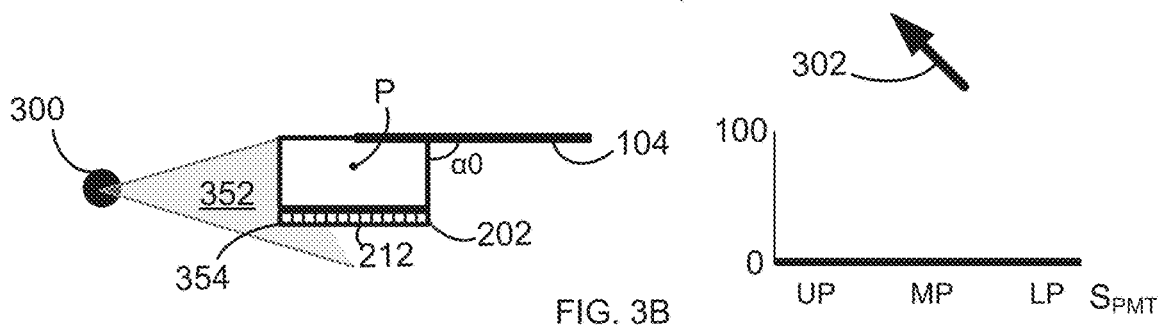
Figure 3C:
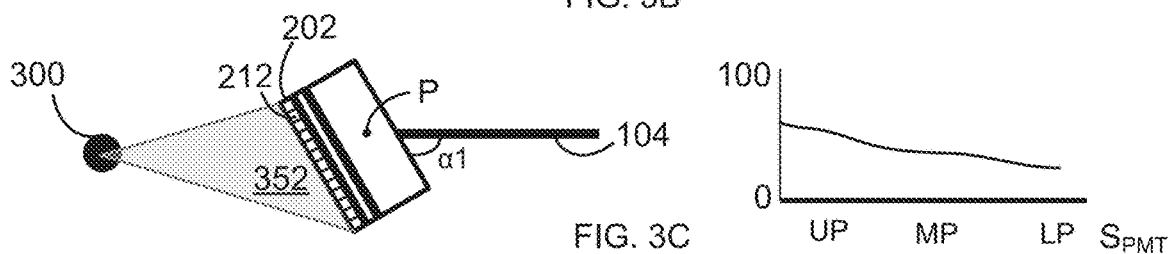
Figure 3D:
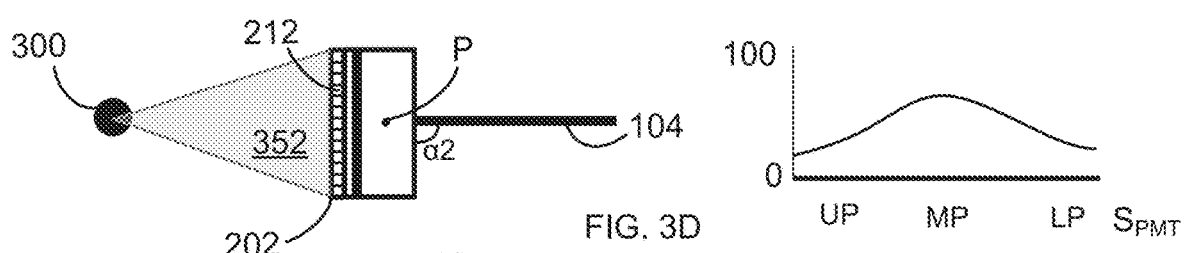
Figure 3E:
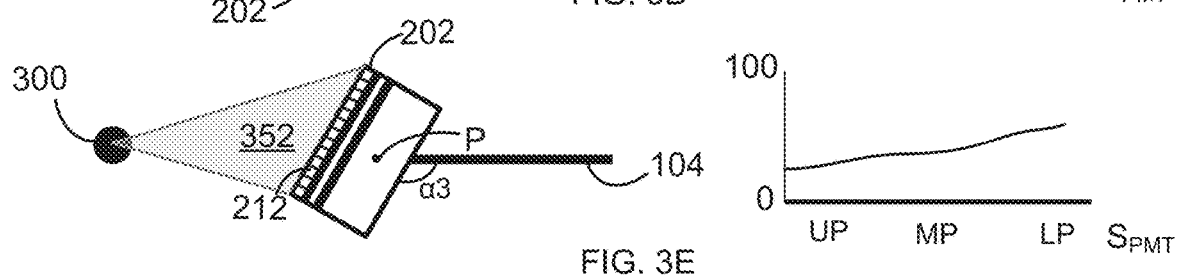
Figure 4:
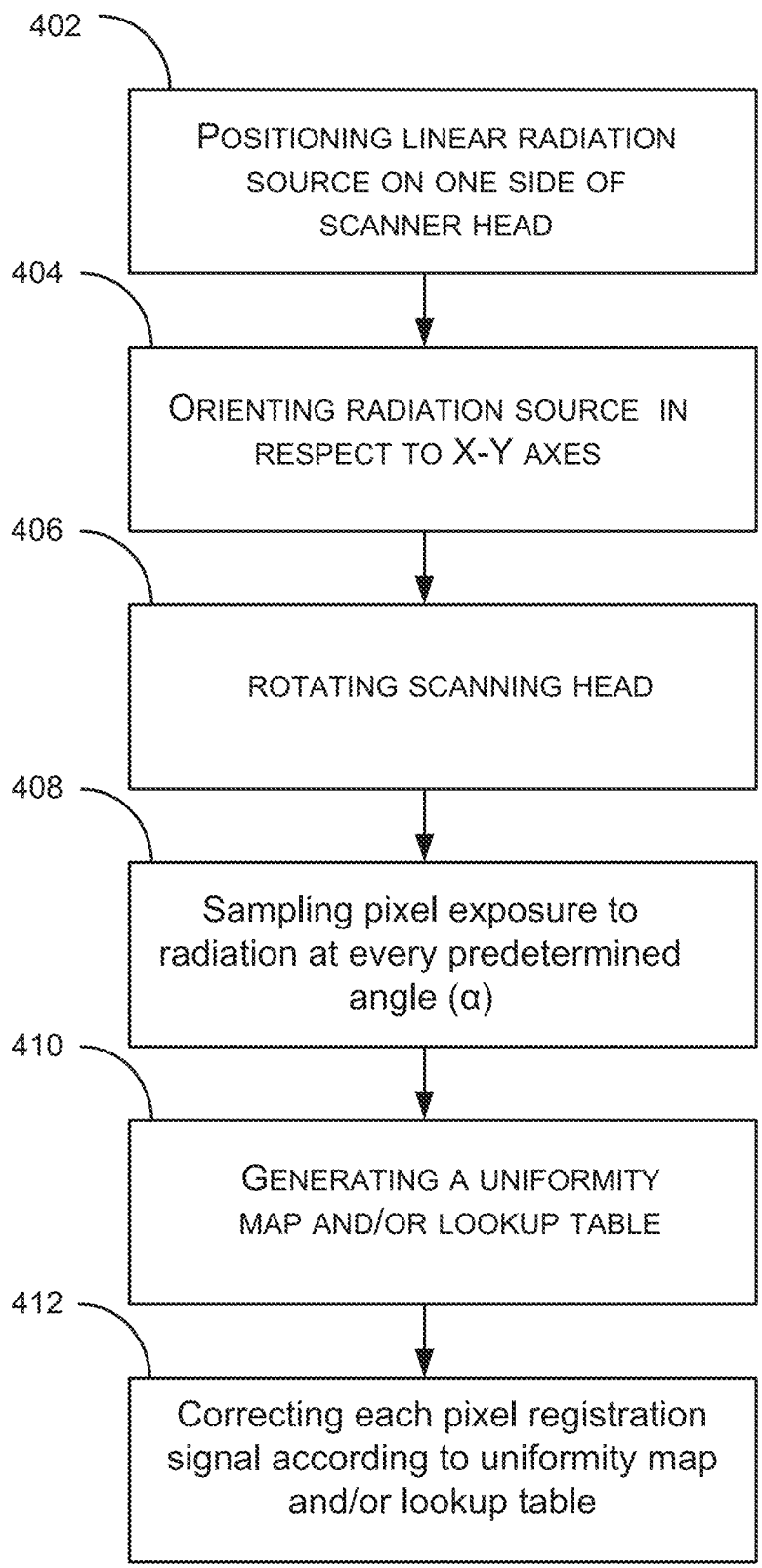
FIG. 4 is which is a flow chart depicting a scanning unit calibration process in accordance with some embodiments of the invention.

Reference is now made to FIGS. 3B-3E which are side view simplified illustrations of the exemplary embodiment of scanning unit 118 shown in FIG. 3A viewed from a direction indicated in FIG. 3A by arrow 302 and respective received signal strength from PMT ($S_{PMT}$) and FIG. 4, which is a flow chart depicting a scanning unit 118 calibration process.

In the embodiment shown in FIGS. 3A-3E, line radiation source 300 is positioned at a distance from scanning unit 118 and oriented in accordance with a given matrix of X and Y coordinates as explained in greater detail elsewhere herein.

In some embodiments, scanning unit 118, which is pivotable about a Center of Rotation (COR), which in FIGS. 3A and 3E comprises longitudinal axis (P), is rotated to an initializing position in which modules 212 arrays 202 are at an angle ($\alpha 0$) (e.g. pivot angle) in respect to a predetermined reference e.g., extendable arms 104 coupled to rotor 112 and registered by encoder 216. Respective graphs depicting received signal strength (e.g., energy level) from PMT ($S_{PMT}$) from an upper portion (UP) through a middle portion (MP) to a lower portion (LP) of modules 212 arrays 202 at each angle ($\alpha$) are also shown.

At an initial angle ($\alpha 0$), as shown in the exemplary embodiment depicted in FIG. 3B, modules 212 are positioned spatially to have no (Zero) exposure to radiation effluence 352 (e.g., parallel to a central effluence beam from source 300). At this stage, a Zero (0) signal is sampled from every module 212 pixel depicted in FIG. 3B as a flat graph at level Zero (0).

In some embodiments, scanning unit 118 is rotated and sampling is performed of modules 212 pixel measuring the level of exposure to emitted radiation effluence 352. In some embodiments and optionally, scanning unit 118 is rotated in a stepwise manner in accordance with predetermined increments, e.g., single degree increments. The exemplary embodiments shown in FIGS. 3C-3E depict three exemplary steps in the rotation of scanning unit 118. In the transition from FIG. 3B to FIG. 3E, scanning unit 118 is rotated in a clockwise manner in respect to COR. However, in some embodiments and as indicated in FIG. 3A by arrow 152, scanning unit 118 is configured to rotate in one or both of clockwise and counterclockwise directions. In some embodiments and optionally, scanning unit 118 pivots in a swiping reciprocating motion. In some embodiments, rotation of scanning unit is oscillatory.

FIG. 3C illustrates scanning unit 118 rotated in a counterclockwise direction from angle ($\alpha 0$) to angle ($\alpha 1$), less than 90 degrees, of arrays 202 in respect to a predetermined reference e.g., extendable arms 104 coupled to rotor 112 and registered by encoder 216. The respective graph shows that modules 212 arrays 202 located at an upper portion (UP) scanner unit 118 emit a stronger signal ($S_{PMT}$) (e.g., energy level) than modules 212 arrays 202 located at other portions (e.g., MP and LP) resulting from angle of impingement of radiation (e.g. photons) on collimator 354.

FIG. 3D, depicts scanning unit 118 after being rotated further in a counterclockwise direction from angle ($\alpha 1$) to angle ($\alpha 2$), equal to 90 degrees, of arrays 202 in respect to a predetermined reference e.g., extendable arms 104 coupled to rotor 112 and registered by encoder 216. The respective graph shows that modules 212 arrays 202 located at an upper portion (MP) scanner unit 118 emit a stronger signal ($S_{PMT}$) (e.g., energy level) than modules 212 arrays 202 located at other portions (e.g., UP and LP) resulting from angle of impingement of radiation (e.g. photons) on collimator 354.

FIG. 3E, depicts scanning unit 118 after being rotated further in a counterclockwise direction from angle ($\alpha 2$) to angle ($\alpha 3$), greater than 90 degrees. E.g., in some embodiments, angle ($\alpha 3$) is greater than 90 degrees. E.g., in some embodiments, an angle between ($\alpha 2$) and ($\alpha 3$) is greater than 90 degrees. Where angle $\alpha x$ (e.g. $\alpha 1$, $\alpha 2$, $\alpha 3$) is of arrays 202 with respect to a predetermined reference e.g., extendable arms 104 coupled to rotor 112 and, in some embodiments, registered by encoder 216. The respective graph shows that modules 212 arrays 202 located at an upper portion (LP) scanner unit 118 emit a stronger signal ($S_{PMT}$) (e.g., energy level) than modules 212 arrays 202 located at other portions (e.g., UP and MP) resulting from angle of impingement of radiation (e.g. photons) on collimator 354.

A potential advantage of rotation of scanning unit 118 about the COR of the scanning unit (e.g. longitudinal axis (P)) is that, by the end of the calibration process, each pixel has been exposed to the same dose of radiation.

A potential advantage is in that in some embodiments and in some situations, calibration of scanning unit 118 using the described process calibrates the COR by correcting for movement inaccuracies (e.g. rotational movement inaccuracies) of scanning unit 118 rotation mechanism, e.g., calibrating mechanical "drift".

Once radiation effluence signals are received and optionally sampled from every module 212 pixel e.g. at predetermined angles of rotation of scanning unit 118 about COR, in some embodiments, one or more of a uniformity map, a uniformity correction matrix and a calibration lookup table are then generated by controller 101 e.g. from pixel signals.

In summary and in reference to FIG. 4, in some embodiments, the scanning unit 118 calibration process comprises:

At 402, positioning one or more line radiation sources 300 on one side of scanning unit 118, and identifying source 300 and scanning unit 118 locations. In some embodiments, a single line radiation source is positioned at a parallel to a COR of the rotor. In some embodiments, the source is secured in to position and/or to the stator by a jig (e.g. as described elsewhere in this document).

At 404, orienting the line radiation source in respect to X-Y axes.

At 406, rotating scanning unit 118 about a scanning unit COR (e.g. axis P) in respect to source 300.

At 408, sampling exposure of pixels (e.g. pixel signals) to radiation effluence emitted by line source 300 at every predetermined angle ($\alpha$) of scanning unit 118 rotation.

At 410, generating a uniformity map and/or a lookup table of photon count read under optimal conditions and/or a uniformity correction matrix.

At 412, correcting each pixel registration signal e.g. by a multiplicative factor for deviations from the lookup table parameters and/or uniformity map and/or a uniformity correction matrix.

Exemplary Scanner Detector Angular Calibration—Single Radiation Source Location

As explained elsewhere herein, in some embodiments, an N-M imaging system includes a plurality of scanning units 118 (e.g., 4, 6, 8, 12, 14) each configured to move independently e.g., to pivot about scanning unit 118 longitudinal axis (P) and/or to rotate about rotor 112 central axis (W). Gantry mechanisms involved in various optional movements of scanning unit 118 are complex and possibly subject to cumulative mechanical "drift". Additionally, differences may exist in a spatial angular orientation of scanning units 118 relative to one another.

The calibration process uses the ability of the detectors to assess the direction of the radiation source 300 from a scanning unit 118 detector. The process corrects for all detected inaccuracies accrued during the mounting of the scanning units 118 on gantry rotor 112 in terms of the rotation about their longitudinal axis (P). In general terms, the inaccuracy accumulated from all detector rotation (e.g. pivot) angles ($\alpha$) is corrected for by assessing the pivot rotation inaccuracy using a single line source and measuring the source direction in respect to scanning units 118 at a plurality of gantry rotation locations.

Figure 5B:
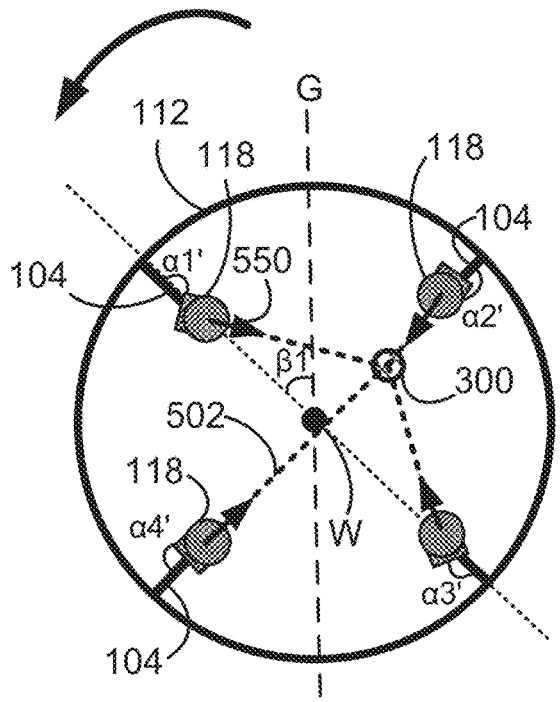
FIGS. 5A, 5B and 5C are simplified diagrams of calibration of relative angular orientation of scanning units in accordance with some embodiments of the invention.
Figure 5A:
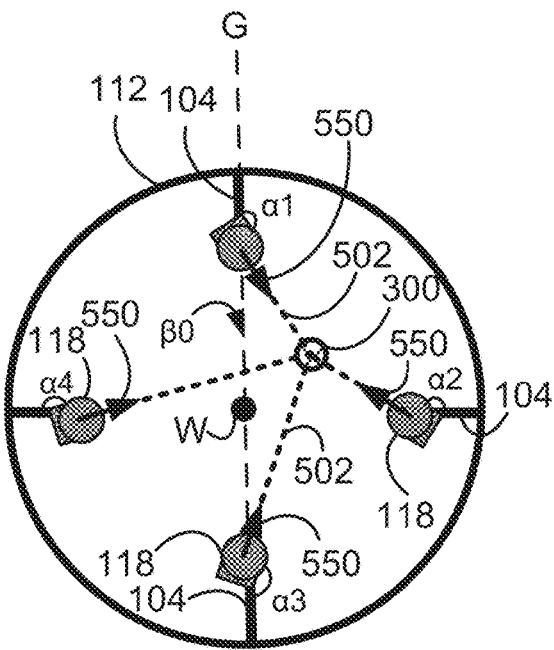
Figure 5C:
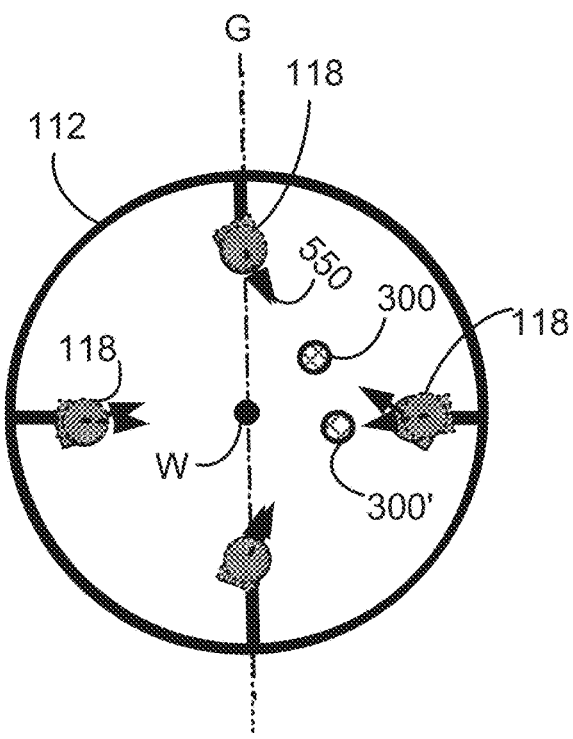
Figure 6A:
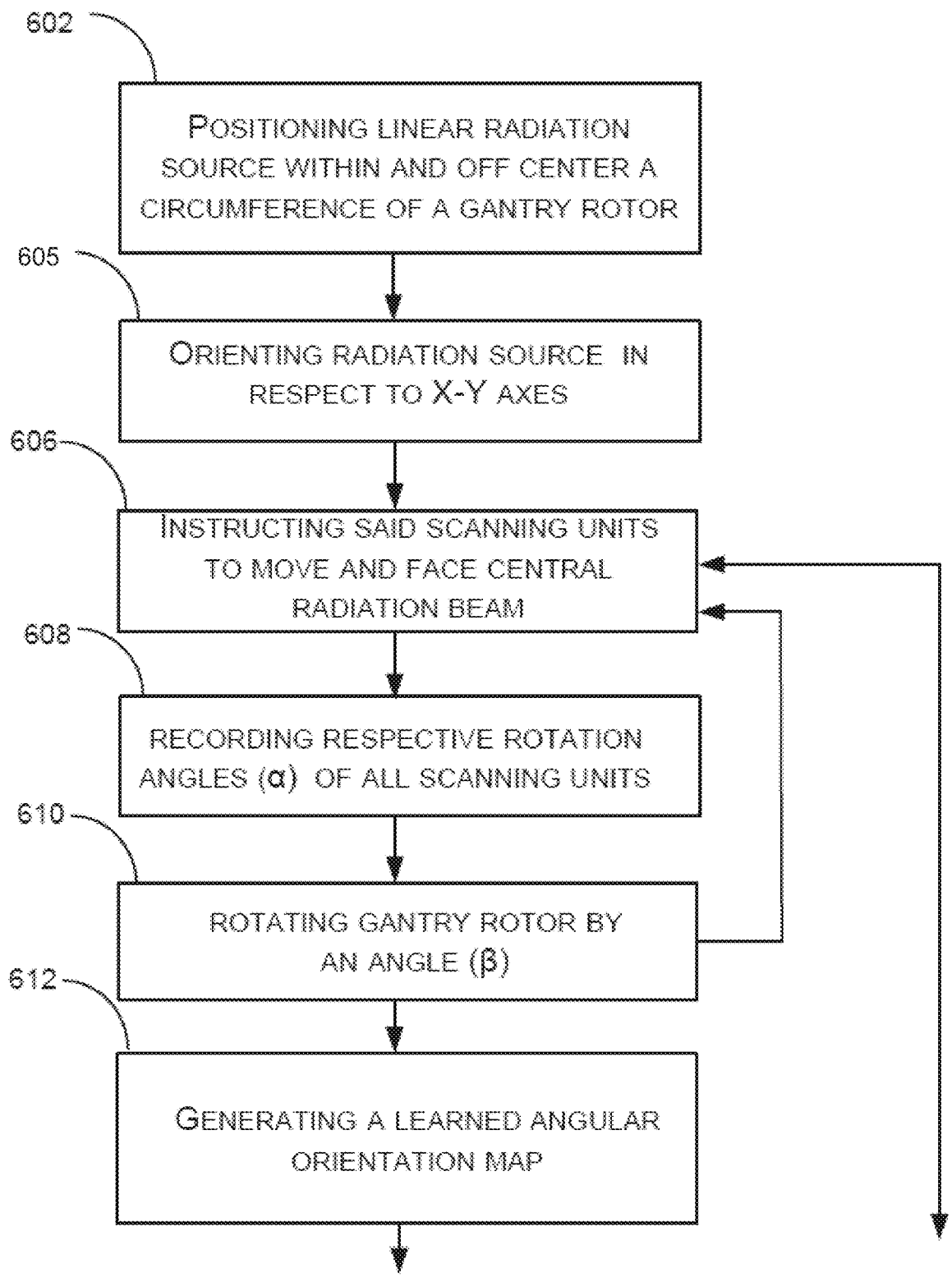
FIGS. 6A and 6B are a flow chart depicting a calibration process of angular orientation of scanning units mounted on a gantry rotor in accordance with some embodiments of the invention.
Figure 6B:
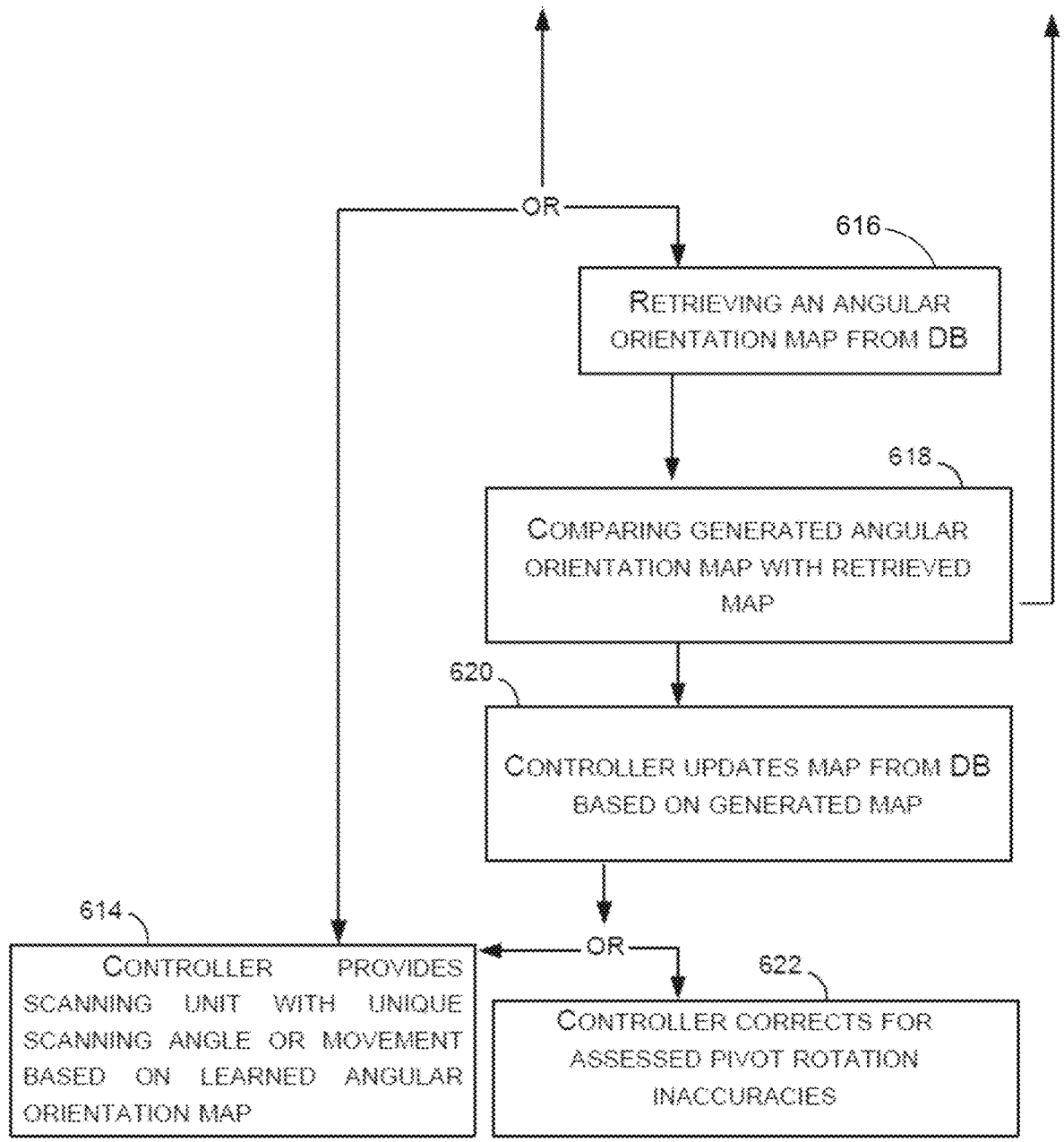

Reference is now made to FIGS. 5A, 5B and 5C, which are simplified diagrams of calibration of relative angular orientation scanning units in accordance with some embodiments of the invention and to FIGS. 6A and 6B, which are a flow chart depicting a calibration process of angular orientation of the scanning units mounted on a gantry rotor in according with some embodiments of the invention.

Calibration of the relative angular direction of one or more scanning detector is necessary to insure angular consistency between all the detector units. For example, ordering all detector unit motors to rotate about axis (P) to a certain angle ($\alpha$), should result in all scanning detectors "looking" in the same direction.

To calibrate the relative angular orientation of one or more of scanning units 118 using the commonly practiced procedures at least two reference points are required and their relative coordinates in space—known. However, in some embodiments, a line source of radiation 300 is used for calibration of both calibrating scanner detector uniformity map and energy resolution, e.g. as explained elsewhere herein, and angular orientation of one or more of scanning units 118 mounted on rotor 112 in respect to each other and to rotor 112.

In the exemplary embodiment shown in FIGS. 5A and 5B a gantry rotor 112 comprises four scanning units 118 positioned at 12 o'clock, 3 o'clock, 6 o'clock and 9 o'clock positons in respect to gantry rotor 112. In the exemplary embodiment depicted in FIG. 5A, gantry rotor 112 is oriented at a "Home" position at an angle ($\beta 0$) in respect to a reference axis (G) wherein in FIG. 5B, gantry rotor 112 has been rotated counter clockwise to an angle ($\beta 1$) in respect to reference axis (G).

In FIG. 5A, a stationary radiation source 300 has been positioned within a circumference of rotor 112, between scanning units 118, off-center, away from rotor 112 COR (central axis (W)) and optionally in parallel to rotor 112 central axis (W). Alternatively, in some embodiments, the source is placed centrally, at central axis W. In some embodiments, source 300 is positioned along the COR. As depicted in FIG. 5A, all scanning unit 118 motors have been signaled by controller 101 to orient scanning units 118 to face source 300 (e.g., scanning unit 118 longitudinal axes in perpendicular to a respective central radiation beams 502 emitted from source 300 as depicted by arrows 550). At this stage respective scanning unit pivot acquisition angles ($\alpha 1$, $\alpha 2$, $\alpha 3$ and $\alpha 4$) reported by respective encoders 216 are recorded by controller 101, e.g. as explained elsewhere herein.

As illustrated in the exemplary embodiment depicted in FIG. 5B, gantry rotor 112 is now rotated in a counter clockwise direction and oriented at an angle ($\beta 1$) from reference axis (G). All scanning unit 118 motors have been instructed and signaled by controller 101 to reorient scanning units 118 to face source 300 (e.g., scanning unit 118 longitudinal axes in perpendicular to a respective central radiation beams 502 emitted from source 300 as depicted by arrows 550. At this stage respective scanning unit pivot acquisition angles ($\alpha 1'$, $\alpha 2'$, $\alpha 3'$ and $\alpha 4'$) reported by respective encoders 216 are recorded by controller 101, e.g. as explained elsewhere herein.

The described process of scanning unit pivot acquisition angles of one or more of scanning units 118 can be repeated for a one or more specific gantry rotation angles ($\beta$) as necessary.

In some embodiments, one or more scanning units 118 are coupled to rotor 112 at designated locations however not all scanning units 118 are necessarily oriented at the same angle ($\alpha$) or in the same direction, e.g., at a radiation source 300 acquisition angle or at a COR acquisition angle. Alternatively and optionally, in some embodiments, all scanning units 118 may be recorded to be oriented at the same angle ($\alpha$) e.g., ($\alpha=0$) however, in reality one or more scanning units 118 have an orientation other than other units 118 or are actually oriented at an angle ($\alpha$) other than ($\alpha=0$).

In some embodiments, controller 101 is configured to learn the differences between recorded and actual angles ($\alpha$) or locations of scanning units 118 in 3D space and input found differences into corrected movement instructions for each individual scanning unit 118. As a result, in some embodiments, paths of movement from a first position (e.g., at a source acquisition angle) to a second position (e.g., at a source acquisition angle) is unique for every scanning unit 118 and differs between scanning units 118.

In some embodiments, controller 101 is configured to receive and process information regarding positioning and unique movement data received from each of the scanning units 118 and generate output information regarding among others for each scanning unit 118: unique path of movement, speed of movement, angular movement, rate of movement, angles ($\alpha 1'$, $\alpha 2'$, $\alpha 3'$ and $\alpha 4'$) recorded during the unique movement, position at angle ($\alpha 0$) and position at a source acquisition angle after at least one rotor rotation along an angle ($\beta 1$) from angle ($\beta=0$) to ($\beta 1$).

Alternatively and optionally, in some embodiments, scanning units 118 are directed by controller 101 to scan or face source 300 and errors derived from the received scanning data (i.e., image or phantom) of erroneously positioned at source acquisition angle scanning unit 118 is recorded and corrected accordingly by controller 101 and/or manually.

FIG. 5C illustrates the gantry of FIG. 5B together with radiation source 300, rotated clockwise by an angular value of angle ($\beta 1$) and super imposed over the gantry of FIG. 5A revealing that by rotating the gantry, an additional virtual source 300' is generated at a different location than the location of the first true source in respect to scanning units 118 and can therefore repeat the calibration process and angular calculations as many times as desired. By calculating the detector angular movement or rotation (a') for several gantry rotation angles (β3) several virtual source 300' locations are generated increasing the angular calibration accuracy.

A potential advantage of angular orientation of one or more of scanning units 118 using a line radiation source as described is in that all scanning units 118 are calibrated at once.

A potential advantage of use of a line radiation source for both scanner detector performance e.g., uniformity map and energy resolution as explained elsewhere herein and angular orientation of one or more of scanning units 118 is in that both calibration processes can be performed optionally sequentially and/or consecutively without removing and reassembling the scanning units 118 onto gantry rotor 112.

A potential advantage of angular orientation of one or more of scanning units 118 using a line radiation source as described is in that scanning units 118 are calibrated in respect to each other and to the rotor 112 obviating the need for a grid-type radiation source arranged by a set of coordinates.

In some embodiments, a line radiation source can be replaced with any two or three dimensional source including at least two distinct points e.g., a cube, a star, a cylinder, a ring, a pyramid and any other source having suitable geometry.

In summary and in reference to FIGS. 6A and 6B, in some embodiments, the calibration process of angular orientation of one or more of scanning units 118 mounted on rotor 112 in respect to each other and to rotor 112 comprises:

At 602, positioning one or more line radiation sources 300 between scanning units 118 within a circumference of a gantry rotor and positioned off-center and away from the rotor COR. In some embodiments, one or more line radiation sources 300 are positioned at the COR.

In some embodiments, at 605, orienting the one or more line radiation sources in respect to X-Y axes.

At 606, controller 101 instructs scanning units 118 to move and face a central beam 502 of source 300, and at 608 recording respective rotation angles (α) of all scanning units 118 reported by encoder 216.

At 610, rotating gantry rotor by an angle (β) and repeating the process from step 606 one or more times.

At step 612, generating an angular orientation map based on the recorded angles (α) and optionally, the recorded angles (α) after one or more rotational movements at angle (β) intervals or during continuous movement of gantry rotor 112 and/or one or more extending arms 104. In some embodiments, step 612 comprises a learning step at which controller 101 learns the angular orientation of one or more scanning units 118 and provides, at step 614, a driving motor (not shown) for one or more scanning units 118 and/or respective arm 104 with a unique scanning angle and/or movement instruction corrected for learned angular orientation of specifically one or more scanning units 118 based on the generated angular orientation map.

Alternatively and optionally, a factory produced angular orientation map is stored in controller 101 database (DB) and, at 616, controller 101 retrieves the stored factory produced angular orientation map and, at 618, compares the generated angular orientation map with the factory produced angular orientation map and, at step 620, controller 101 updates the factory produced angular orientation map according to the generated angular orientation map.

Optionally, at step 622, controller assesses scanning units 118 angular orientation inaccuracies and corrects for assessed inaccuracies.

Alternatively and optionally, controller 101 provides, at step 614, a driving motor (not shown) of one or more scanning units 118 and/or respective arm 104 with a unique scanning angle and/or movement instruction corrected for updated angular orientation map for specifically one or more scanning units 118 based on the updated angular orientation map.

In some embodiments, the calibration process (e.g., generation of an angular orientation map) is performed on three levels of complexity of movement and orientation:

a) A low level of complexity for example, controller 101 provides one or more N-M imaging device 100 component (e.g. extending arm 104) with instructions to move from a length (L1) to a length (L2).

b) A medium level of complexity, form example controller 101 provides one or more N-M imaging device 100 component (e.g. scanning unit 118) with instructions to scan in a given direction.

c) A high level of complexity, for example controller 101 provides one or more N-M imaging device 100 component (e.g. scanning unit 118) with instructions to scan an area in coordination with an adjacent same component.

As explained in greater detail elsewhere herein, controller 101 is configured to collected data from all levels of the calibration process and generate an angular orientation map of scanning units 118.

In some embodiments, movement of scanning units 118 defined and instructed by controller 101 results in one or more scanning units 118 moving concurrently in a same direction at a same speed. In some embodiments, movement of scanning units 118 defined and instructed by controller 101 results in unique movement of one or more scanning units 118 moving concurrently or and different times, in a same or different directions at a same or different speed.

In some embodiments, an angular orientation map stored in the database (DB) is an angular orientation map generated during a previous calibration session.

A potential advantage of angular orientation of one or more of scanning units 118 using a line radiation source as described is in that one or more scanning units 118, one or more extending arms 104 and/or rotor 112 move mat the same time and are calibrated at once.

A potential advantage of angular orientation of one or more of scanning units 118 using a line radiation source as described is in that controller 101 receives and learns information regarding a movement and orientation unique to each and every scanning unit 118 from any first position at a source acquisition angle to any second position at a source acquisition angle. In some embodiments, the controller 101 is configured to use the learned information to correct controller 101 moving and positioning instructions provided to each scanning unit 118 driving system that are specific and unique to each and every scanning unit in accordance with the learned received information.

Figure 7A:
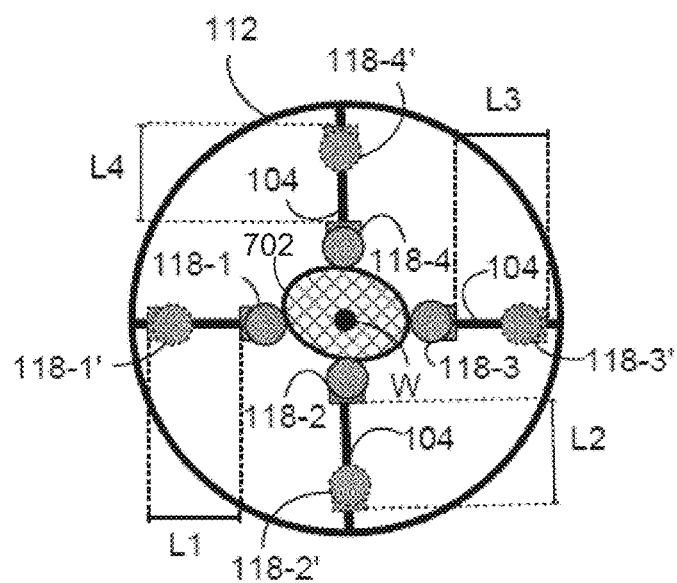
FIGS. 7A, 7B, 7C and 7D are simplified diagrams of calibration of relative angular orientation scanning units in accordance with some embodiments of the invention.
Figure 7B:
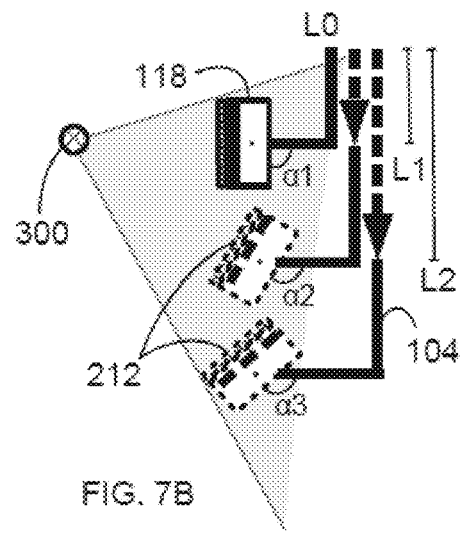
Figure 7C:
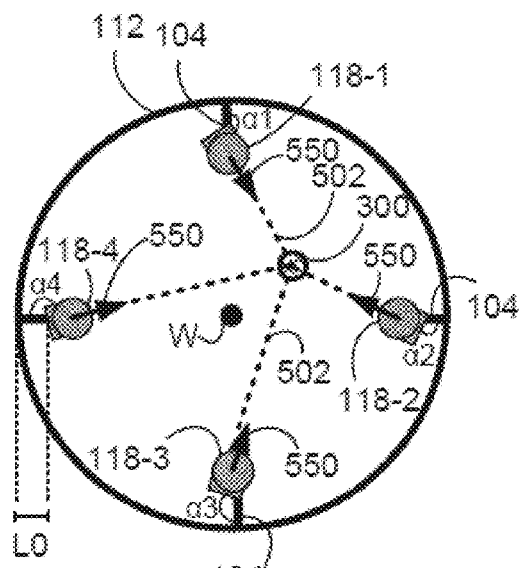
Figure 7D:
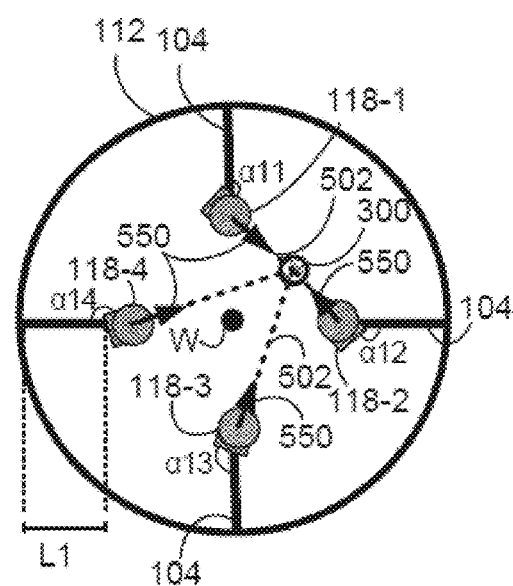
Figure 8:
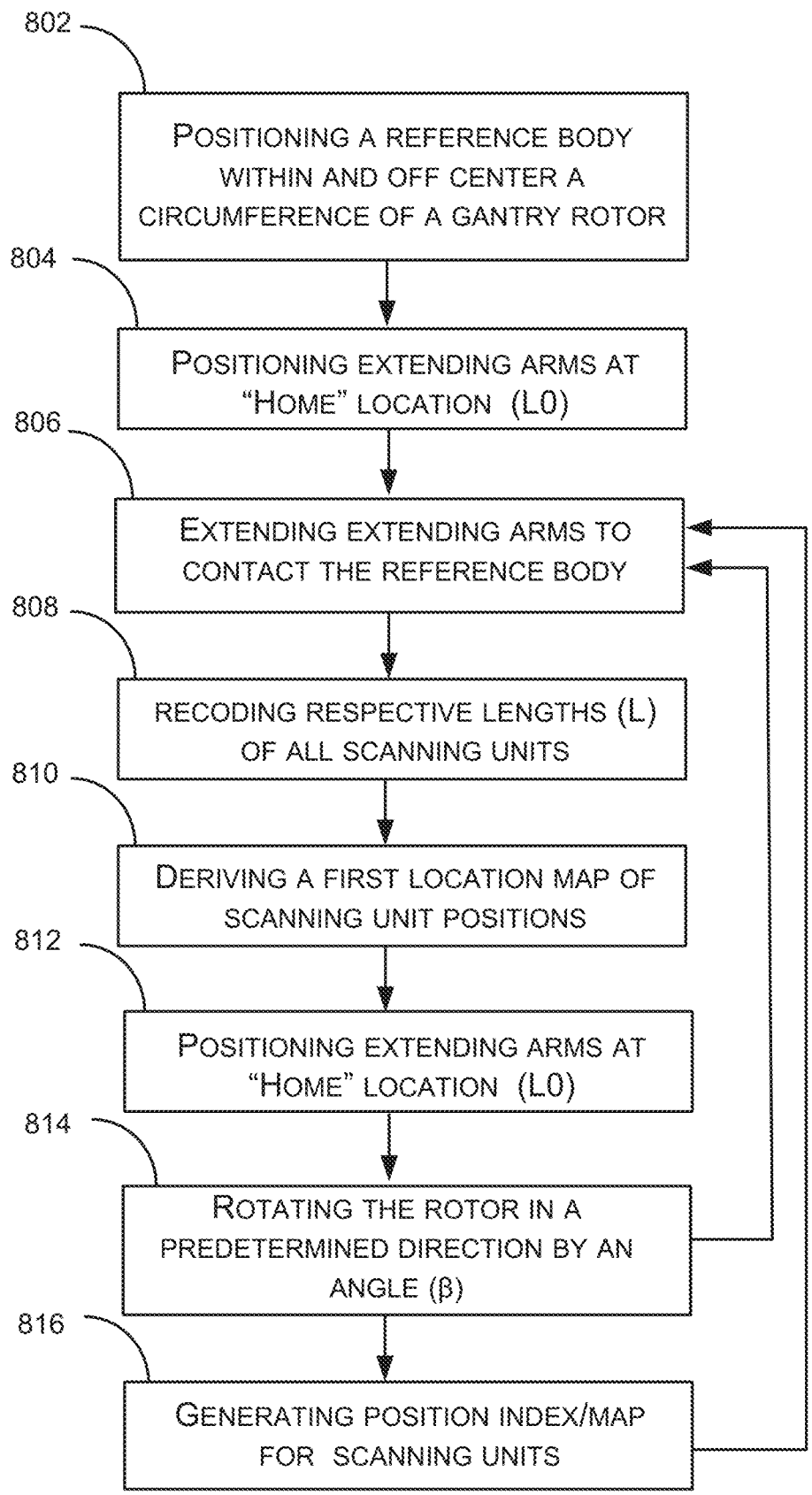
FIG. 8 is a flow chart depicting a calibration process of angular orientation of the scanning units mounted on a gantry rotor in according with some embodiments of the invention.

Reference is now made to FIGS. 7A, 7B, 7C and 7D, which are simplified diagrams of calibration of relative angular orientation scanning units in accordance with some embodiments of the invention and to FIG. 8, which is a flow chart depicting a calibration process of angular orientation of the scanning units mounted on a gantry rotor in according with some embodiments of the invention.

In some embodiments, calibration of scanning units 118 spatial position is performed mechanically as shown in the exemplary embodiment illustrated in FIG. 7A in conjunction with FIG. 8. In some embodiments, the calibration is carried out by positioning a reference body 702 (e.g., physical obstacle) having known dimensions inside a perimeter of gantry rotor 112. In some embodiments, reference body 702 comprises a symmetrical cross-section. In some embodiments, physical reference body 702 comprises an asymmetrical cross-section.

In summary and in reference to FIG. 8, in some embodiments, the mechanical calibration process of the spatial position at a source acquisition angle of one or more of scanning units 118 mounted on rotor 112 in respect to each other and to rotor 112 comprises at 802 positioning one or more reference bodies 702 inside a perimeter of gantry rotor 112 at a known location (known X, Y, Z coordinates).

In some embodiments, a calibration process includes:

At 804, positioning all extending arms 104 at their respective "Home" positions (L0).

At 806, extending the extending arms 104 until scanning units 118 are in contact with, or at a predetermined distance from, one or more reference bodies 702.

At 808, obtaining from each extending arm encoder an extension length (L1, L2, L3 and L4) of each of respective scanning units 118-1/118-2/118-3 and 118-4 from their respective "Home" positions 118-1'/118-2'/118-3' and 118-4' and at 810 deriving a first location map of scanning unit position at a source acquisition angles.

At 812, positioning all extending arms 104 at their respective "Home" positions (L0) and rotating rotor 112 at 814 by an angle (β) and repeating the process from step 806 one or more times as necessary. At 816 using controller 101 and generating a location index for all scanning units.

At 816, generating a location index using controller 101 for each component driving motor position (e.g., gantry rotor 112 rotation, extending arm 104 radial motion) of the exact location and angular orientation of scanning units 118 at every angle (β) of rotor 112 and extension length (L) of extending arms 104.

In some embodiments, optionally and as explained elsewhere herein, a scanning unit 118 array 202 is positioned initially at an angle (α0) in respect to line radiation source 300 (e.g., as shown in FIG. 3A) and a Zero (0) signal is sampled from every module 212 pixel.

As depicted in FIG. 7B, in some embodiments, activation of extending arm 104 continuously or in a stepwise manner changes the location of the position of scanning unit 118 in respect to line radiation source 300. In some embodiments, scanning unit 118 is signaled by controller 101 to home-in on line radiation source 300 bringing scanning unit 118 rotation motor (not shown) to change rotation angle (α) e.g., from (α1) through (α2) to (α3). In some embodiments, angle (α) at each extension length (L0, L1, L2) of extending arm 104 is recorded.

In FIG. 7C, a stationary radiation source 300 has been positioned between scanning units 118, off-center, away from rotor 112 COR (central axis (W)) and optionally in parallel to rotor 112 central axis (W). As depicted in FIG. 7C, all scanning units 118 are positioned at a "Home" location in which extending arms 104 are at their shortest length (L0) all scanning unit 118 motors have been signaled by controller 101 to orient scanning units 118-1, 118-2, 118-3 and 118-4 to face source 300 (e.g., scanning unit 118 longitudinal axes in perpendicular to a respective central radiation beams 502 emitted from source 300 as depicted by arrows 550). At this stage respective scanning unit pivot acquisition angles (α1, α2, α3 and α4) reported by respective encoders 216 are recorded by controller 101 as explained elsewhere herein.

As illustrated in the exemplary embodiment depicted in FIG. 7D, extending arms 104 have been extended to a length of (L1). All scanning unit 118 motors have been signaled by controller 101 to reorient scanning units 118 to face source 300 (e.g., scanning unit 118 longitudinal axes in perpendicular to a respective central radiation beams 502 emitted from source 300 as depicted by arrows 550). At this stage respective scanning unit new pivot acquisition angles (α11, α12, α13 and α14) reported by respective encoders 216 are recorded by controller 101 as explained elsewhere herein.

The described process of scanning unit pivot acquisition angles of one or more of scanning units 118 can be repeated for a one or more specific extending arms extended lengths (L) as necessary.

Figure 9A:
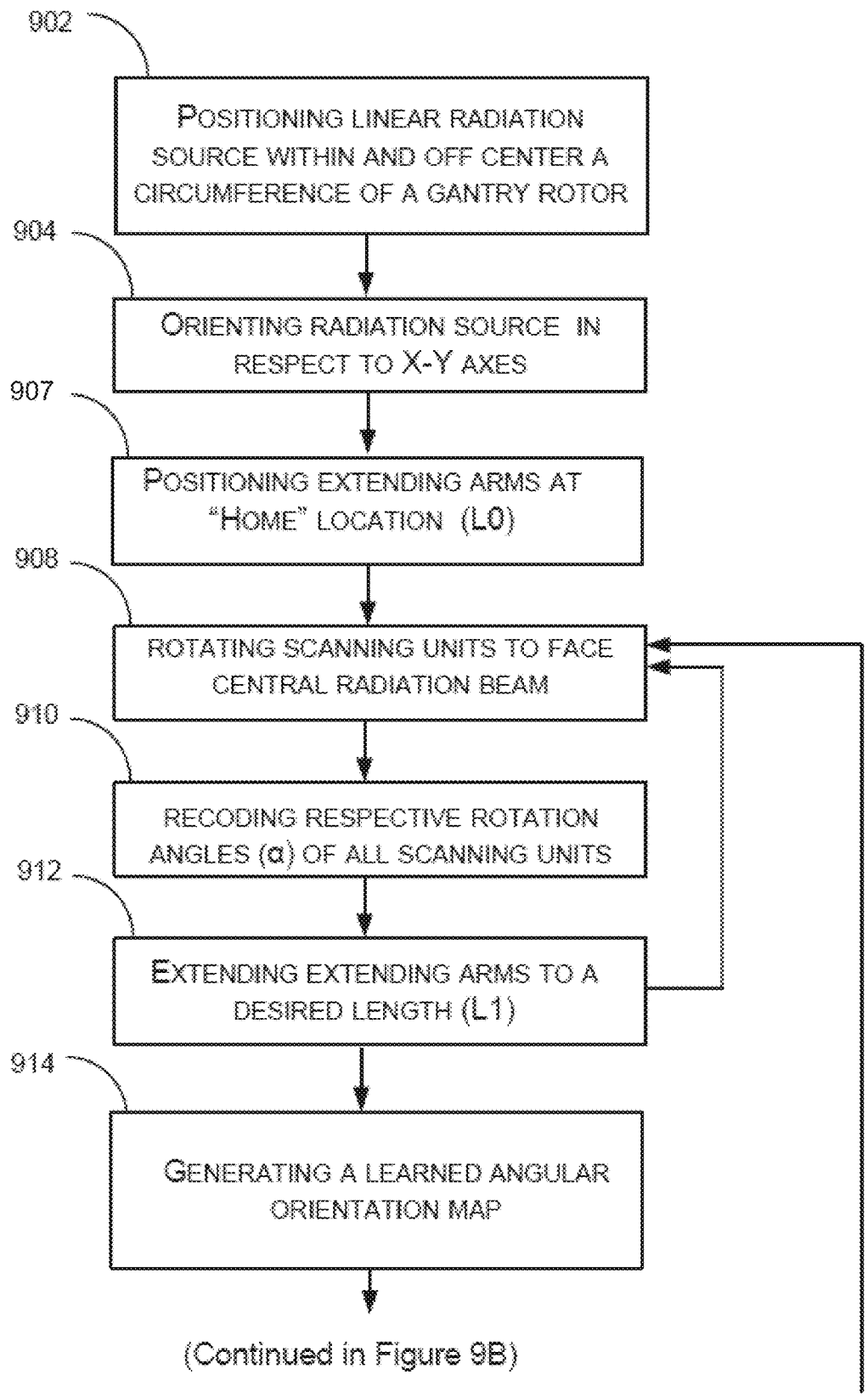
FIGS. 9A and 9B are a flow chart depicting a process of angular orientation of scanning units mounted on a gantry rotor in according with some embodiments of the invention.
Figure 9B:
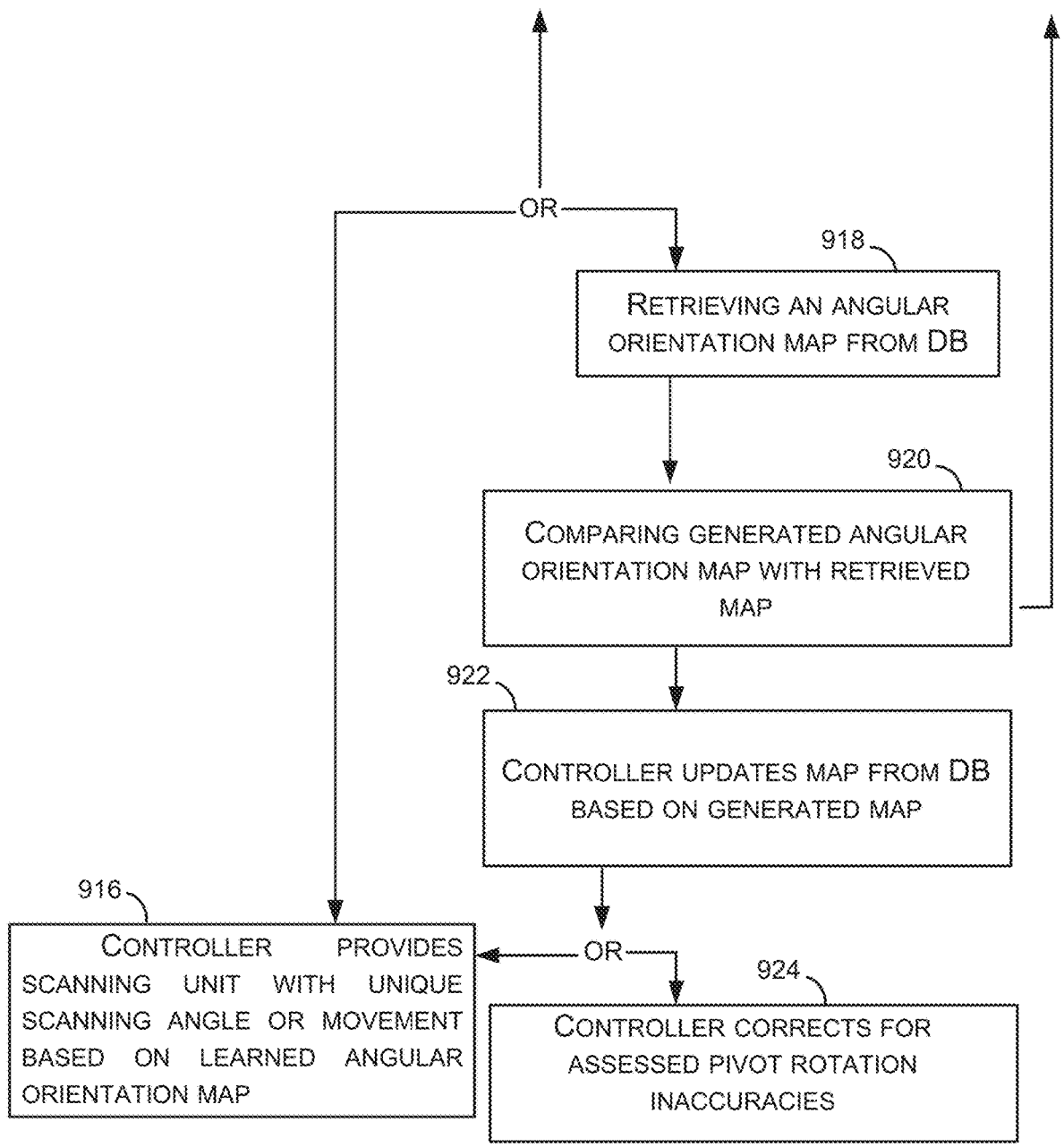

In summary and in reference to FIGS. 9A-9B, which is a flow chart depicting a calibration process of angular orientation of the scanning units mounted on a gantry rotor in according with some embodiments of the invention.

In some embodiments, the calibration process of angular orientation of one or more of scanning units 118 mounted on rotor 112 in respect to each other and to rotor 112 comprises:

At 902, positioning one or more line radiation sources 300 within a circumference of a gantry rotor and positioned between scanning units 118, off-center and away from the rotor COR. Alternatively, in some embodiments, the source is placed centrally, e.g. at central axis W.

At 904, orienting the line radiation source in respect to X-Y axes.

At 907, positioning extending arms 104 at a "Home" location (L0).

At step 908, controller 101 instructs scanning units 118 to move and face a central beam 502 of source 300, and at 910 recording respective rotation angles (α) of all scanning units 118 reported by encoder 216.

At 912 extending the extending arms 104 to a desired length (L1) and repeating the process from step 908.

At step 914 generating an angular orientation map based on the recorded angles (α) and optionally, the recorded angles (α) after one or more stepped intervals at various lengths (L) or during continuous movement of gantry extending arms 104.

In some embodiments, step 914 comprises a learning step at which controller 101 learns the angular orientation of one or more scanning units 118 and provides at step 916 a driving motor (not shown) for one or more scanning units 118 and/or respective arm 104 with a unique scanning angle and/or movement instruction corrected for learned angular orientation of specifically one or more scanning units 118 based on the generated angular orientation map.

Alternatively and optionally, a factory produced angular orientation map is stored in a database (DB) and at 918 controller 101 retrieves the stored factory produced angular orientation map and at 920 compares the generated angular orientation map with the factory produced angular orientation map and at step 922, controller 101 updates the factory produced angular orientation map according to the generated angular orientation map.

Optionally, at step 924, controller assesses scanning units 118 angular orientation inaccuracies and corrects for assessed inaccuracies. Alternatively and optionally, controller 101 provides at step 916 a driving motor (not shown) of one or more scanning units 118 and/or respective arm 104 with a unique scanning angle and/or movement instruction corrected for updated angular orientation map for specifically one or more scanning units 118 based on the updated angular orientation map.

In some embodiments, an angular orientation map stored in the database (DB) is an angular orientation map generated during a previous calibration session.

In some embodiments, movement of scanning units 118 defined and instructed by controller 101 results in one or more scanning units 118 moving concurrently in a same direction at a same speed. In some embodiments, movement of scanning units 118 defined and instructed by controller 101 results in unique movement of one or more scanning units 118 moving concurrently or and different times, in a same or different directions at a same or different speed. A potential advantage of angular orientation of one or more of scanning units 118 using a line radiation source as described is in that all scanning units 118 (e.g., 2 units, 4 units, 6 units, 8 units, 10 units, 12 units, 14 units or more than 14 units) are calibrated at once without removing and reassembling the scanning units 118 onto gantry rotor 112.

A potential advantage of use of a line radiation source for both scanner detector uniformity map and energy resolution as explained elsewhere herein and angular orientation of one or more of scanning units 118 is in that both calibration processes can be performed optionally sequentially and/or consecutively without removing and reassembling the scanning units 118 onto gantry rotor 112.

A potential advantage of angular orientation of one or more of scanning units 118 using a line radiation source as described is in that scanning units 118 are calibrated in respect to each other and to the rotor 112 obviating the need for a grid-type radiation source arranged in accordance with a set of coordinates.

A potential advantage of angular orientation of one or more scanning units 118 using a line radiation source as described is in that one or more scanning units 118, one or more extending arms 104 and/or rotor 112 move mat the same time and are calibrated at once.

In some embodiments, a line radiation source can be replaced with any two or three dimensional source including at least two distinct points e.g., a cube, a star, a cylinder, a ring, a pyramid or any other source having suitable geometry. Alternatively and optionally, the radiation source comprises a point radiation source continuously moving along a linear path of movement.

Exemplary Mechanical and Motor Calibration e.g. with Micron Tracker

In some embodiments, a N-M imaging system comprises a plurality of mechanically moving components (e.g., scanning unit 118, extending arm 104, gantry rotor 112 and patient table). Mechanical calibration enables correction for errors stemming from mechanical inaccuracies (e.g. mechanical "drift" and/or differences between various movable couplings and joints). By mapping the location of a scanning detector unit 118 for each component driving motor position (e.g., gantry rotor 112 rotation, extending arm 104 radial motion) a location index is generated by controller 101 of the exact location, orientation and pivot axis of scanning units 118 at every angle ($\beta$) of rotor 112, angle ($\alpha$) of scanning unit 118 and extension length (L) of extending arms 104.

Figure 10A:
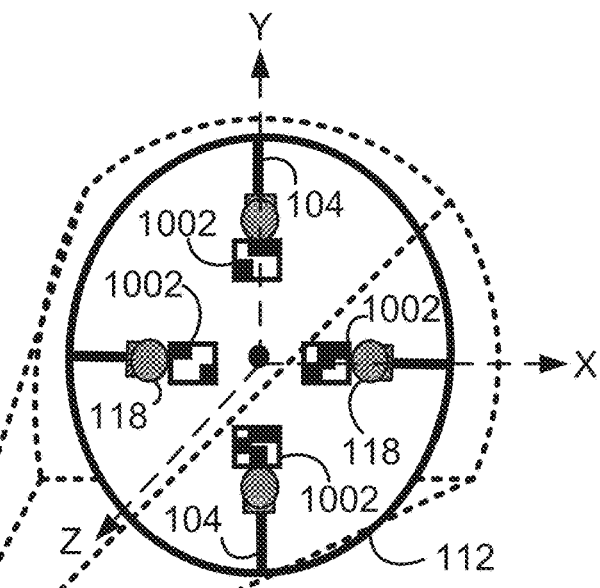
FIGS. 10A and 10B are perspective view simplified illustrations of a N-M imaging system calibration in accordance with some embodiments of the invention.
Figure 10A:
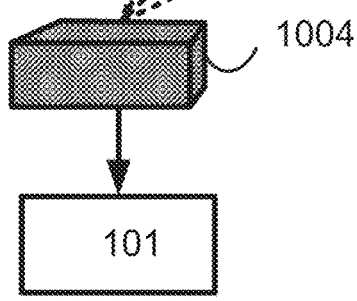
Figure 10B:
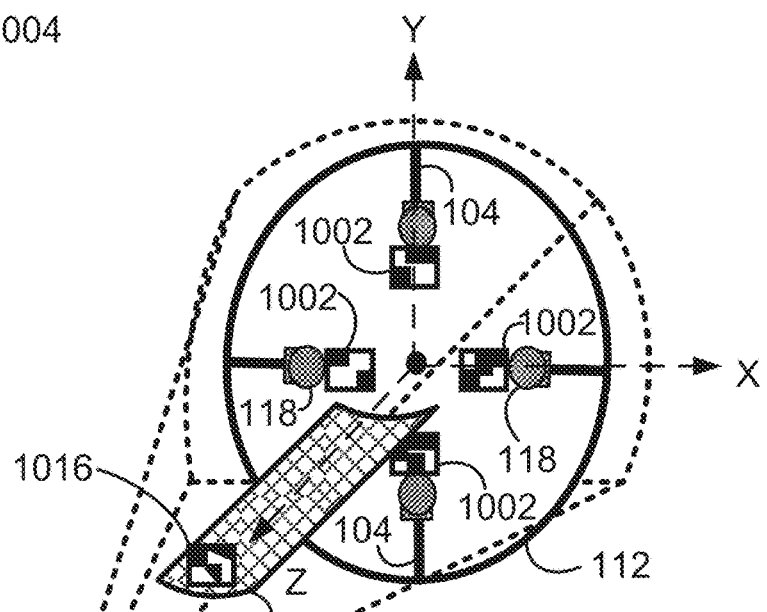
Figure 10B:
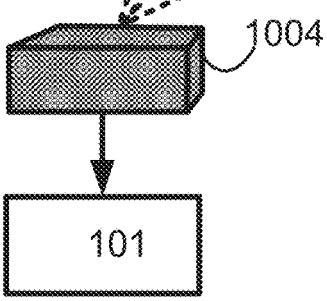

Referring now to FIGS. 10A and 10B, which are perspective view simplified illustrations of a N-M imaging system calibration in accordance with some embodiments of the invention: As shown in FIG. 10A, tracking tags 1002 are attached to each scanning unit 118 and an external localization tracker 1004 (e.g., a micron tracker) measures a location of each scanning unit 118 in reference to three dimensional X, Y, and Z coordinates in primarily in respect to a plurality of rotor 112 rotation angles ($\beta$). The result for each scanning unit 118 is a result calibrating the cumulative effect of movement of all mechanical couplings, joints and driving motor output axes.

In some embodiments and as shown in FIG. 10B, N-M imaging system includes a patient table 1006 configured to move in axes X, Y and Z each movement controlled by a separate mechanical driving system and a separate encoder encoding movement along one or more of axes X, Y and Z. In some embodiments, patient table 1006 includes one or more tracking tags 1016. In the exemplary embodiment depicted in FIG. 10A, mechanical calibration of includes generation of a location index by controller 101 for each component driving motor position (e.g., gantry rotor 112 rotation, extending arm 104 radial motion) of the exact location, angular orientation and pivot axis of scanning units 118 at every angle ($\beta$) of rotor 112, angle ($\alpha$) of scanning unit 118 and extension length (L) of extending arms 104 in respect to one or more locations and orientations of patient table 1006.

In some embodiments, external localization tracker 1004 comprises 3D camera e.g., Kinect™.

Exemplary Calibration Using a N-M Scan Pattern Design (E.G. Focusing, ROI Centric) E.G. in Accordance with Known Location of Scanning Units.

Once location of scanning units 118 is known and recorded as explained elsewhere herein, the recorded information can be used to construct (e.g. a safe and/or accurate) N-M Region of Interest (ROI) centric scan pattern design.

Figure 11:
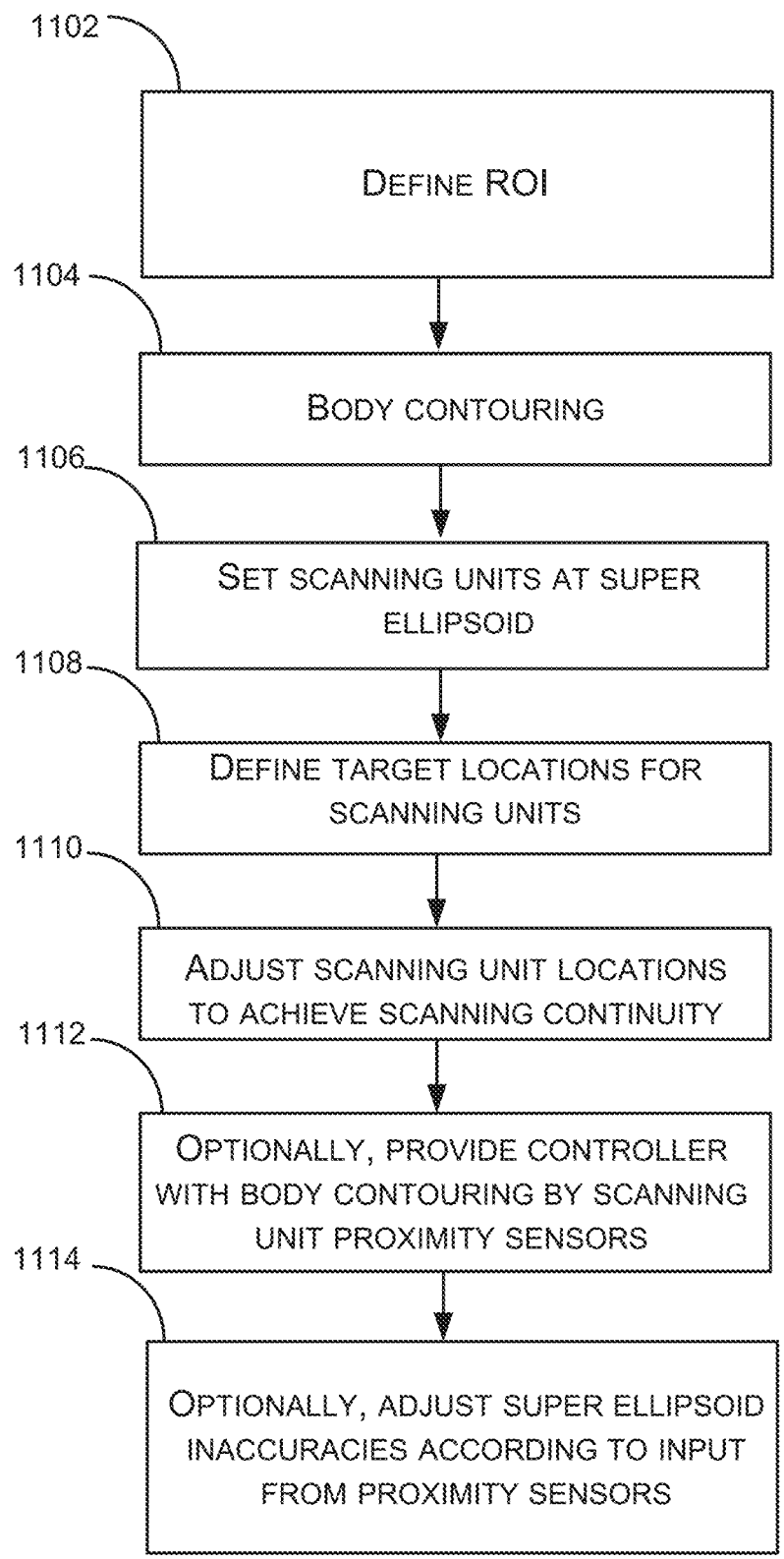
FIG. 11 is a flow chart depicting construction process of a N-M Scan pattern design in accordance with some embodiments of the invention.

Reference is now made to FIG. 11, which is a flow chart depicting construction process of a N-M Scan pattern design in accordance with some embodiments of the invention.

Initially at 1102, a primary ROI (e.g. polygon ellipse or super ellipsoid shaped ROI) is defined that outlines an enclosure in which emitted radiation can be detected limiting scanning to the defined primary ROI only. Commonly, an ROI includes one or more Objects of Interest (OOI) e.g., a suspected tumor, which require closer examination. Hence, in some cases one or more OOIs are defined that allow for more focused scan efforts on the object of interest. In some embodiments a ROI is selected, based on location and/or geometry of one or more OM.

In some embodiments, one method of generating a N-M Region of Interest (ROI) centric scan pattern design comprises body contouring, at 1104, by an N-M scan pattern design using 1D or 2D resolution rapid recovery reconstruction aided e.g., by the detector location position at a source acquisition angle recorded information, 3D body contouring, CT scan or a reconstruction of the photon count data. The reconstruction may be of low quality, e.g., radio tomographic reconstruction and in some instances can be used to overly the scan ROI on the reconstruction phantom image.

In some embodiments a second method comprises body contouring using an N-M Scan pattern design according to detectors location. This entails initially performing body contouring by moving one or more scanning units radially inwards until a scanned object (e.g., a human body) is sensed (e.g., by using one or more of Power Spectral Density (PSD), capacitance measurement, proximity sensor/s). Additional gantry rotor rotations can be performed as necessary to get additional body contouring sample points.

In some embodiments, once body contouring information is acquired, locations of all scanning units 118 are set, at 1106, to fit a super ellipsoid encompassing the body contour and, at 1108, target locations for scanning units 118 to move to are defined.

In some instances and, at 1110, a gap between two scanning units 118 is filled by moving a scanning unit 118 in between the two scanning units into position (e.g. within the gap). For example, generating a continuity of scanning units 118 scanning area around the patient.

In some embodiments, and optionally, at 1112, one or more scanning units 118 comprise one or more proximity sensors (not shown) which provide controller 101 with information input regarding proximity of a scanning unit 118 to the scanned body. For example, in some embodiments, proximity sensor data of one or more scanning unit and/or proximity detector (e.g. to the scanned body) are used to construct a body contour.

In some embodiments, and at 1114, in cases in which the super ellipsoid model is inaccurate in respect to the body contour (e.g., patient anatomy), target locations for scanning units 118 are adjusted in accordance with the input provided by the one or more scanning units 118 one or more proximity sensors.

Exemplary interference and Noise Measurement

In some embodiments, the calibration procedures described in detail herein are performed in a stationary or stepped manner movement of N-M imaging system 100. In some embodiments, the calibration procedures are performed in a dynamic state in during movement (e.g., continuous movement) of one or more N-M imaging system 100 components (e.g., rotor 112, scanning units 118 and/or extending arm 104). Dynamic calibration corrects in some embodiments for interferences and distortions stemming from linear and/or angular movement, noise (e.g., generated by vibrations) and/or direction of movement.

Optionally and in some embodiments, following generation of an angular orientation map produced during a dynamic calibration session controller 101 is configured to collect data regarding the measured noise and distortion and input the collected data into a reconstruction process and generate a correcting probability of error index e.g., during algorithmic reconstruction of an image. In some embodiments, such estimation includes probability calculations of correctness and accuracy of received PMT signal ($S_{PMT}$).

In some embodiments, optionally and in reference to FIG. 3B, positioning scanning unit 118 at angle ($\alpha$)=zero (0) in respect to line source 300 provides information regarding environmental noise as well as scattering. As described elsewhere herein, a received PMT signal ($S_{PMT}$) with scanning unit 118 positioned at angle ($\alpha$)=zero (0) is expected to be Zero (no signal). Any signal emitted from scanning unit 118 is measured and attributed to noise originating from e.g., thermal radiation, environmental arbitrary radiation and/or scattering and recorded by controller 101 for input into a generated calibration map and/or index.

Additionally and optionally, in some embodiments, controller 101 generates a map of radiation scatter based on e.g., level of radiation energy indicative also of angle of impingement on modules 212 arrays 202.

A potential advantage of the calibration procedures described herein is in that all calibration processes are performed with the collimators 354 in place (i.e., assembled) and/or removed.

Exemplary Balance of an N-M Imaging System

As explained elsewhere herein, in some embodiments, the N-M imaging system 100 comprises a plurality of moving parts driven (e.g. by motors and pulleys) and comprises a plurality of scanning units coupled to a rotating rotor via extendable arms.

In some embodiments, at least a portion of the disclosed N-M imaging system components are designed to enable the use of a low-friction slew bearing enabling a low power motor to drive gantry 100 rotor 112, potentially increasing accuracy and/or safe control of the moving parts:

a) Reduction of size and weight—lessening the size and weight of the components coupled directly or indirectly to rotor 112 e.g., miniaturized scanning units 118. A central high Voltage power supply is replaced in N-M imaging system 100 by small individual power supplies each located on a dedicated extending arm 604.

b) In some embodiments, extending arms 104 include counter weight/s. In some embodiments, each counter weight balances the weight distribution along extending arm 104 as well as the weight distribution over rotor 112. A potential advantage of using counter weight/s is in that it allows for use of smaller extending arm 104 driving system motor/s. A potential advantage of counter weight is in that, for example, in a case of power outage, the arm balanced by counter weight remains in place or only moves slightly. A potential advantage of counter weight is that it allows manual moving (e.g., pushing back to a "Home" position e.g. in case of emergency or power outage) without the need for excessive force.

c) One or more scanning unit 118 and extending arm 104 motion-controllers (FIG. 1) each coupled to rotor 112 adjacent a detection unit coupling 116 and communicating with controller 101 and scanning unit 118 and extending arm 104 driving systems. Motion controllers 122 control the movement of scanning unit 118 and extending arm 104 in respect to rotor 112 and other scanning units 118 and extending arms 104 and among others ensures movement maintains a balanced gantry.

d) As explained in greater detail elsewhere herein, rotor 112 rotates only partially which enables simpler balancing processes. Additionally and optionally, gantry rotation motion being mostly counter balanced potentially enables use one or more of: small and compact motion system/s, smooth movement of N-M imaging system component/s, movement in small increments, easy manual movement in case of emergency.

Exemplary Quality Control Procedures

The same calibration settings, processes and techniques using a line radiation source as described in greater detail elsewhere herein are used in some embodiments for quality control (QC) purposes. E.g., calibration processes comprising generation of a scanning detector uniformity map, energy resolution calibration, calibration of detector spatial orientation and structural or mechanical calibration are used in some embodiments, for quality control (QC) procedures on a daily, weekly, monthly and/or yearly basis without dismantling the N-M system or repeating the procedure for scanning head.

In some embodiments, the combination of a line radiation source and one or more pivoting scanning units 118 negate the need for Planar Source QC procedures. Procedures such as generation of a scanning detector uniformity map and energy resolution calibration can be used for extrinsic spatial resolution measurements, extrinsic and intrinsic uniformity measurements (with and/or without a collimator), detector and/or detector array calibration (PMT gains, energy, linearity and uniformity, generation of a uniformity correction matrix) and collimator integrity. In some embodiments, detector spatial angular orientation and structural or mechanical calibration procedures including rotation of the gantry rotor 112 and axial extension and retraction of extending arms 104 can be used for QC procedures such as SPECT acquisition by all scanning units 118, reconstruction of acquired SPECT images, intrinsic and uniformity corrections, COR corrections, spatial resolution and orbit (angular) SPECT acquisition (e.g., 90 degree, 180 degree acquisitions).

As in the calibration techniques described herein, in some embodiments, QC procedures using the same described techniques are configured to examine overall SPECT N-M imaging system 100 performance (e.g., separate and cumulative performance of scanning units 118) concurrently and with a single line source of radiation.

A potential advantage of use of detector spatial orientation and structural or mechanical procedures using a line radiation source as described for QC procedures is in that all scanning units 118 are tested at once.

A potential advantage of use of a line radiation source for both scanner detector uniformity map and energy resolution and angular orientation of one or more of scanning units 118 for QC procedures is in that both procedures can be performed optionally sequentially and/or consecutively without removing and reassembling the scanning units 118 onto gantry rotor 112.

A potential advantage of angular orientation of one or more of scanning units 118 using a line radiation source as described is in that QC of scanning units 118 performance in respect to each other and to the rotor 112 obviates the need for a grid-type radiation source arranged by a set of coordinates.

A potential advantage of the QC procedures described herein is in that all QC processes are performed with the collimators 354 in place (i.e., assembled) or removed.

Exemplary Line Radiation Source Jig

Reference is now made to FIGS. 12A, 12B, 12C and 12D, which are perspective and plan view simplified illustrations of a line source jig in accordance with some embodiments of the invention.

As shown in the exemplary embodiment shown in FIG. 12A a line radiation source 300 Jig 1200 comprises an arm 1202 having a coupling 1204 at one end configured to couple jig 1200 to a stationary portion (e.g., stator) of N-M imaging system 100 and a line source 300 holder plate 1206 at a second opposite end.

In some embodiments, line source 300 holder plate 1206 includes one or more line source 300 positioning bores 1208 sized to receive an end of one or more line sources 300. Additionally and optionally, and as shown in FIG. 12B, which is a plan view of the back of jig 1200 viewed from a direction indicated in FIG. 12A by an arrow 1250, holder plate 1206 is coupled to arm 1202 by one or more screws 1210/1212 configured to enable adjustment of holder plate 1206 along a Y-axis e.g., from position (Y1) to position (Y2) and vice versa. In some embodiments, jig 1200 holder plate 1206 is adjustable by one or more adjusting screws 1214.

Referring back to FIG. 12A, one or more adjusting screws 1214 are configured to adjust a tilt angle ($\delta$) of a long axis of line source 300 in reference to a predetermined X-axis. In some embodiments, the position of line source 300 is adjusted along a Y-axis by repositioning line source 300 from a bore 1208 to a bore 1208' distanced from bore 1208 along the Y-axis as depicted in the exemplary embodiment shown in FIG. 12C by an arrow 1252.

Figure 12D:
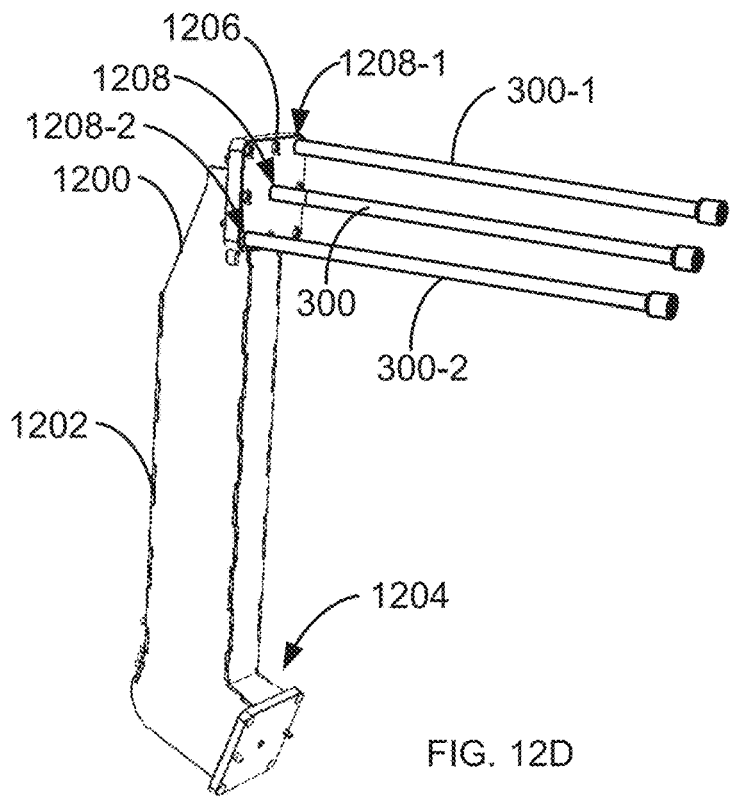

As shown in the exemplary embodiment depicted in FIG. 12D, in some embodiments, jig 1200 holder plate 1206 is configured to hold a plurality of line sources 300. In some embodiments, holder plate 1206 is configured to hold between 1 and 10 line sources 300, between 2 and 8 line source 300, between 4 and 6 line sources 300 or any number of line source 300 in between in one or more spatial configurations. In the exemplary embodiment shown in FIG. 3D, jig 1200 holds three line sources 300, 300-1 and 300-2. In some embodiments, line sources 300, 300-1 and 300-2 emit radiation having the same wavelength. In some embodiments, each of line sources 300, 300-1 and 300-2 emits radiation having a different wavelength. In some embodiments, two or more line sources 300, 300-1 and 300-2 emit radiation having the same wavelengths.

In some embodiments, controller 101 is configured to receive and process information regarding positioning and unique movement data from each of the scanning units 118 in respect to the plurality of line sources and generate output information regarding, among others, for each scanning unit 118: unique path of movement, speed of movement, angular movement, rate of movement, angles ($\alpha1'$, $\alpha2'$, $\alpha3'$ and $\alpha4'$) recorded during the unique movement, position at angle ($\alpha0$) and position at a source acquisition angle after at least one rotor rotation along an angle ($\beta1$) from angle ($\beta=0$) to ($\beta1$).

In the exemplary embodiment depicted in FIG. 12D, line source 300 holder plate 1206 optionally comprises nine positioning bores 1208 arranged in three columns and three rows. Line sources 300, 300-1 and 300-2 are positioned in an optional diagonal pattern in respective positioning bores 1208, 1208-1 and 1208-2 however any other positioning pattern is possible and dependent on the number and arrangement of positioning bores 1208 in holder plate 1206.

Figures 13A, 13B:
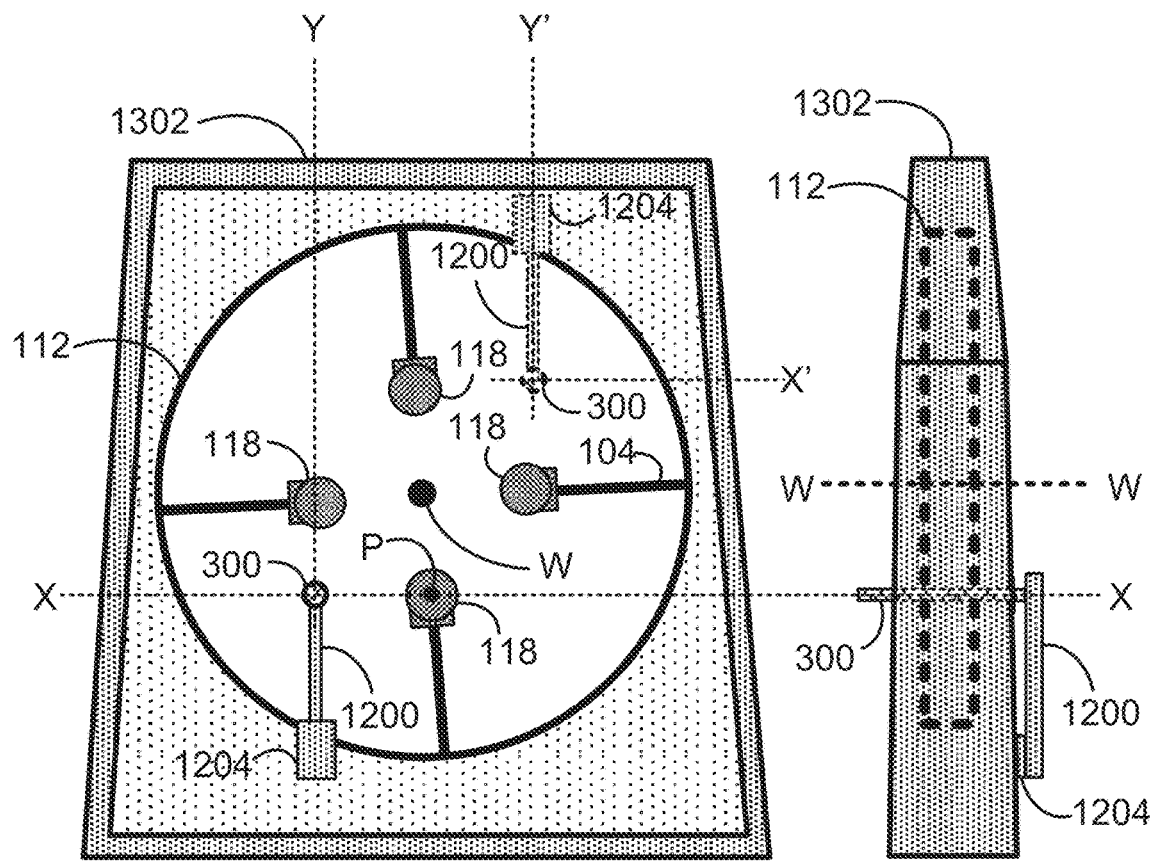
FIGS. 13A and 13B are plan view and side view of implementation of a line source jig in an N-M imaging system in accordance with some embodiments of the invention.

Referring now to FIGS. 13A and 13B, collectively referred to as FIG. 13, which are plan view and side view of implementation of a line source jig in an N-M imaging system in accordance with some embodiments of the invention. As shown in FIG. 13, jig 1200 is configured to be attached via coupling 1204 to a stationary portion of an N-M imaging system gantry 1302 (e.g., a stator) at a known location. For example, in the embodiment shown in FIG. 13, jig 1200 is coupled to stationary portion 1302 placing radiation line source parallel to gantry rotor 112 COR (W) (i.e., perpendicular to the plane of the drawing sheet) at known coordinates (X) and (Y). In some embodiments, the radiation source (e.g. radiation line source) is positioned at the gantry rotor 112 COR.

In some embodiments, once Jig 1200 is positioned at a position with known reference coordinates, the longitudinal axis of line source 300 is then adjusted and calibration and QC procedures are performed as described elsewhere herein. In some embodiments, positioning of line source 300 can be changed to other positioning bores 1208 without dismantling jig 1200 or, alternatively and optionally, jig 1200 is detached from stationary portion 1302 at coordinates (X,Y) and positioned in another location e.g., at coordinates (X', Y'). Optionally, jig 1200 is positioned such that line source 300 is at gantry rotor 112 COR.

General

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method for calibrating a scanning unit in a nuclear medicine (N-M) imaging system, said method comprising:
   a. providing a scanning unit which is pivotable at a mounting location about a center of rotation (COR), said scanning unit including at least one array of detector modules;
   b. positioning at least one radiation source at a predetermined distance from said scanning unit and at a predetermined orientation relative to said scanning unit;
   c. positioning said scanning unit at predetermined initializing position in which said at least one array of detector modules are at an initial pivot angle with respect to said mounting location, wherein at said initial pivot angle said at least one array of detector modules is spatially positioned to have no exposure to radiation effluence (zero $S_{PMT}$) from said at least one radiation source;
   d. sampling pixel exposure of said at least one array of detector modules to measure a first level of said radiation effluence when said at least one array of detector modules is at said initializing position;
   e. recording said predetermined initializing position of said scanning unit and said measured first level of exposure of said at least one array of detector modules to said radiation effluence when said at least one array of detector modules is at said initializing position;
   f. rotating said scanning unit about said COR to a second predetermined position, in which said at least one array of detector modules is at a second pivot angle with respect to the mounting location;
   g. sampling pixel exposure of said at least one array of detector modules to measure a second level of said radiation effluence when said at least one array of detector modules is at said second position;
   h. recording said predetermined second position of said scanning unit and said measured second level of exposure of said at least one array of detector modules to said radiation effluence when said at least one array of detector modules is at said second position;
   i. repeating said rotating (f) of said scanning unit to a new predetermined position, different from any previous predetermined position at which said sampling pixel exposure [action (g)] was performed, until radiation effluence signals have been sampled from every module pixel at said predetermined pivot angles;
   j. generating, for said scanning unit, one or more of a uniformity map, a uniformity correction matrix and a calibration lookup table of photon count from said first and second levels of exposure of said at least one array of detector modules to said radiation effluence when said at least one array of detector modules is at said predetermined positions (c, f, and i); and
   k. calibrating said detector array of said scanning unit by correcting a registration signal for each of said pixels of each said detector array in accordance with said one or more of a uniformity map, a uniformity correction matrix and a calibration lookup table of photon count.

2. The method of claim 1, wherein said at least one radiation source includes at least one line radiation source.

3. The method of claim 2, wherein in said predetermined orientation a single line radiation source of said at least one line radiation source is positioned in parallel to said COR.

4. The method of claim 1, wherein in said predetermined orientation said at least one array of detector modules is oriented in parallel to said radiation effluence.

5. The method of claim 1, wherein said calibrating said detector array {action (k)] includes calibrating all said detector modules of said array of said scanning unit at once.

6. The method of claim 1, wherein said N-M imaging system includes an encoder configured to measure movement of said scanning unit and wherein said recording (e and h) includes receiving and recording said encoder data.

7. The method of claim 1, wherein said rotating said scanning unit [action (f)] includes rotating said scanning unit in a stepwise manner in accordance with predetermined increments.

8. The method of claim 7, wherein said predetermined increments are single degree increments.

9. The method of claim 1, wherein said scanning unit is configured to rotating in at least one of a clockwise direction and a counterclockwise direction.

10. The method of claim 9, and wherein said rotating [action (f)] includes rotating said scanning unit in one of a swiping reciprocating motion and an oscillatory motion.

11. The method of claim 1 wherein, after said repeating, each said pixel has been exposed to a same dose of radiation.

12. The method of claim 1, wherein said correcting includes correcting a registration signal for each said pixel by a multiplicative factor for deviations from said one or more of a uniformity map, a uniformity correction matrix and a calibration lookup table.

13. The method of claim 1, wherein said N-M imaging system comprises a gantry rotatable about a gantry COR, a plurality of said scanning units mounted to said gantry.

14. The method of claim 13, wherein N-M imaging system includes a plurality of arms configured to extend toward and away from said gantry COR, wherein each of said plurality of scanning units is mounted to said gantry by a respective arm of said plurality of arms.

15. The method according to claim 1, wherein said recording (e and h) each comprises receiving and recording encoder data.

16. The method according to claim 1, wherein each said detector array is arranged along at least one surface of said scanning unit.

17. The method according to claim 1, wherein said sampling pixel exposure of said at least one array of detector modules to said emitted radiation (d and g) includes measuring pixel signals from said detector array.

18. The method according to claim 1, wherein said scanning unit is configured to pivot about a longitudinal axis.

19. The method according to claim 1, further including generating information regarding detector performance.

20. The method according to claim 19, wherein said detector performance includes energy resolution.

21. The method according to claim 1, wherein said scanning unit is moveable in at least two dimensions.

22. The method according to claim 21, wherein said at least two dimensions include at least one rotational direction and at least one translational direction.

23. The method according to claim 1, wherein said at least one source emits isotropic radiation.

24. The method according to claim 1, wherein said at least one array of detector modules comprises Cadmium Zinc Telluride (CZT) detectors.

\* \* \* \* \*